US012570660B2

(12) United States Patent
Skead et al.

(10) Patent No.: US 12,570,660 B2
(45) Date of Patent: Mar. 10, 2026

(54) PROCESS FOR THE PREPARATION OF A PYRIMIDINO-DIAZEPINE DERIVATIVE

(71) Applicant: CYCLACEL LIMITED, London (GB)

(72) Inventors: Benjamin Skead, Cambridge (GB); Derek Londesbrough, Hartlepool (GB); Michal Czyzewski, Durham (GB); Chris Atherton, Durham (GB); Chris Gill, Sedgefield (GB); Alex Hudson, Gateshead (GB)

(73) Assignee: CYCLACEL PHARMACEUTICALS, INC, London (GB)

( * ) Notice: Subject to any disclaimer, the term of this patent is extended or adjusted under 35 U.S.C. 154(b) by 1028 days.

(21) Appl. No.: 17/634,693

(22) PCT Filed: Aug. 14, 2020

(86) PCT No.: PCT/GB2020/051950
§ 371 (c)(1),
(2) Date: Feb. 11, 2022

(87) PCT Pub. No.: WO2021/032958
PCT Pub. Date: Feb. 25, 2021

(65) Prior Publication Data

US 2022/0289755 A1 Sep. 15, 2022

(30) Foreign Application Priority Data

Aug. 16, 2019 (GB) ..................................... 1911796
Jun. 8, 2020 (GB) ..................................... 2008591

(51) Int. Cl.
*C07D 487/04* (2006.01)

(52) U.S. Cl.
CPC ................................. *C07D 487/04* (2013.01)

(58) Field of Classification Search
None
See application file for complete search history.

(56) References Cited

U.S. PATENT DOCUMENTS

2010/0075973 A1 3/2010 Cao et al.
2012/0184543 A1 7/2012 Tang et al.
(Continued)

FOREIGN PATENT DOCUMENTS

CA 2696261 A1 * 2/2009 .......... A61K 31/495
EP 2481739 A1 8/2012
WO WO 2004/058776 A1 7/2004
(Continued)

OTHER PUBLICATIONS

PubChem 1-Methylpiperazine, "1-Methylpiperazine", https://pubchem.ncbi.nlm.nih.gov/compound/53167, create date Mar. 26, 2005, accessed May 27, 2025 (Year: 2006).*
(Continued)

*Primary Examiner* — Noble E Jarrell
(74) *Attorney, Agent, or Firm* — Brian C. Trinque; Lathrop GPM LLP

(57) ABSTRACT

In one aspect, the invention relates to a process for preparing a compound of formula (XII), wherein PG is a protecting group, or a compound of formula (XI), comprising the steps of: (i) treating a compound of formula XIII, wherein PG is a protecting group, with N-methylpiperazine to form a compound of formula XII, wherein said compound of formula XII is in the form of a mixture of cis and trans isomers; (ii) combining the mixture formed in step (i) with an organic solvent and heating the solvent mixture so formed; (iii) isolating the trans-isomer of the compound of formula XII from the solvent mixture formed in step (ii); and (iv) optionally treating said trans-isomer of the compound of formula XII with an acid to form a compound of formula XI; and isolating said compound of formula XI. Further aspects of the invention relate to processes for preparing pyrimido-diazepinone derivatives using the above process and intermediates.

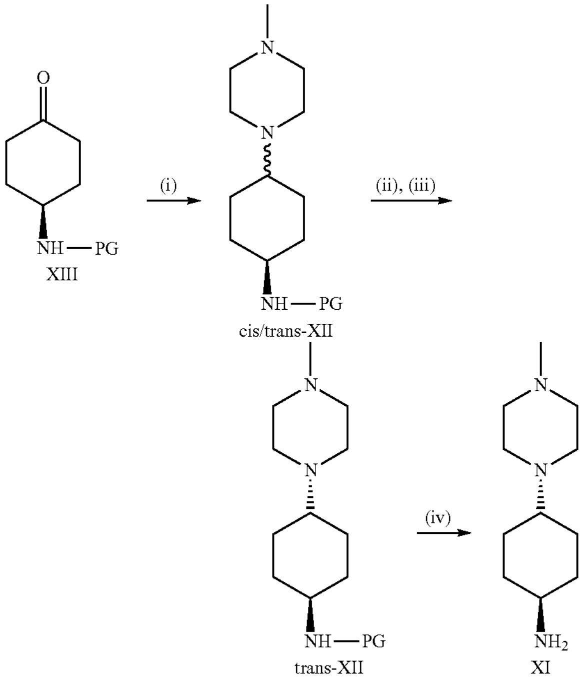

XIII
cis/trans-XII
trans-XII
XI

20 Claims, No Drawings

(56) References Cited

U.S. PATENT DOCUMENTS

| | | | |
|---|---|---|---|
| 2015/0175541 A1 | 6/2015 | Takayama et al. | |
| 2017/0066780 A1 | 3/2017 | Dominguez et al. | |

FOREIGN PATENT DOCUMENTS

| | | | |
|---|---|---|---|
| WO | WO 2004/067000 A1 | 8/2004 | |
| WO | WO 2006/040281 A1 | 4/2006 | |
| WO | WO 2007/087250 A2 | 8/2007 | |
| WO | WO2009/040556 A1 | 4/2009 | |
| WO | WO 2010/025073 A1 | 3/2010 | |
| WO | WO 2011/017561 A1 | 2/2011 | |
| WO | WO 2013/033246 A2 | 3/2013 | |
| WO | WO 2015/058163 A2 | 4/2015 | |
| WO | WO 2018/005860 A1 | 1/2018 | |
| WO | WO-2019136244 A1 * | 7/2019 | ............. A61K 35/00 |

OTHER PUBLICATIONS

Greene. Protective Groups in Organic Synthesis, Third Edition, 1999, 494-503 (Year: 1999).*

Berge et al., "Pharmaceutical Salts", *Journal of Pharmaceutical Sciences* 66(1):1-19 (1977).

Degenhardt et al., "Targeting Polo-like Kinase in Cancer Therapy", *Clinical Cancer Research* 16(2):384-389 (2010).

Greene et al, "Protective Groups in Organic Chemistry", Wiley, Second Edition (1991).

Harrison et al., Compendium of Organic Synthetic Methods, John Wiley and Sons, vol. 1-8 (ISBN 047135550X) (1971).

Kanaji et al., "Expression of Polo-Like Kinase 1 (PLK1) Protein Predicts the Survival of Patients with Gastric Carcinoma", *Oncology* 70(2):126-133 (2006).

Schöffski et al., "A phase I, dose-escalation study of the novel Polo-like kinase inhibitor volasertib (BI 6727) in patients with advanced solid tumours", *European Journal of Cancer* 48(2):179-186 (2012).

Spänkuch et al., "Rational combinations of siRNAs targeting Plk1 with breast cancer drugs", *Oncogene* 26(39):5793-5807 (2007).

Takaki et al., "Polo-like kinase 1 reaches beyond mitosis—cytokinesis, DNA damage response, and development", *Current Opinion Cell Biology* 20(6):650-660 (2008).

International Search Report and Written Opinion for PCT International Patent Application No. PCT/GB2020/051950, mailed Sep. 25, 2020.

* cited by examiner

PROCESS FOR THE PREPARATION OF A PYRIMIDINO-DIAZEPINE DERIVATIVE

The present invention relates to a process for preparing a pyrimido-diazepinone derivative, and intermediates useful therein.

BACKGROUND TO THE INVENTION

Polo-like kinases are a family of serine threonine kinases that are critical regulators of cell cycle progression and DNA damage responses (Petronczki et al, Curr Opin Cell Biol. 2008 December; 20(6):650-60). PLK1 is frequently overexpressed in cancer and its level correlates with aggressiveness and has prognostic value for predicting outcome (Kanaji et al. Oncology. 2006; 70(2):126-33). Cancer cell proliferation is blocked in vitro and in vivo by small molecule PLK1 inhibitors and PLK1 antisense/siRNA (Spankuch et al, Oncogene, 2007 Aug. 23; 26(39):5793-807). PLK1 inhibitors cause mitotic arrest and subsequent induction of apoptosis. Due to the central role of PLK1 in mitosis and cell division, rapidly proliferating normal cells are also affected by PLK1 inhibitors. As a result clinical PLK1 inhibitors have shown narrow therapeutic windows, and have been shown to cause significant haematological toxicity (Schoffski et al, Eur J Cancer, 2012 January; 48(2):179-86). Identification of patient/tumour selection markers and treatment regimens which will extend the therapeutic window is critical for the successful development of these agents. It has been shown that mutant TP53 can be one such predictive marker for sensitivity towards PLK1 inhibitors (Degenhardt et al, Clin Cancer Res. 2010 Jan. 15; 16(2):384-9).

Small molecule benzthiazole-3-oxide PLK1 inhibitors and their use in the treatment of proliferative disorders are described in International patent application WO 2004/067000 in the name of Cyclacel Limited. In addition, a series of pyrimido-diazepinone molecules has also been shown to potently and selectively inhibit PLK1 (see International patent application WO 2009/040556; Cyclacel Limited), demonstrating strong anti-proliferative activity in vitro and in vivo.

Compound I, also known as 4-((9'-cyclopentyl-5'-methyl-6'-oxo-5',6',8',9'-tetrahydrospiro-[cyclopropane-1,7'-pyrimido[4,5-b][1,4]diazepin]-2'-yl)amino)-3-methoxy-N-((trans)-4-(4-methylpiperazin-1-yl)cyclohexyl)benzamide, or 4-(9'-cyclopentyl-5'-methyl-6'-oxo-5',6',8',9'-tetrahydrospiro[cyclopropane-1,7'-pyrimido[4,5-b][1,4]diazepine]-2'-ylamino)-N((trans)-4-(4-methylpiperazin-1-yl)cyclohexyl)-3-methoxybenzamide, was first disclosed in WO 2009/040556 and has the structure shown below:

I

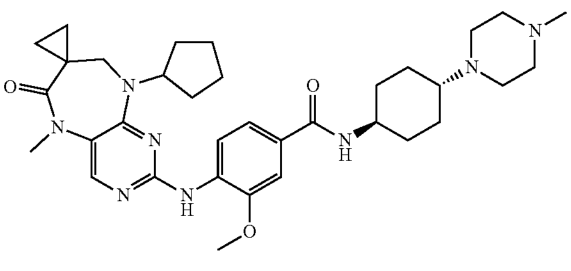

Studies have demonstrated that compound I is a potent inhibitor of polo-like kinase 1 (PLK1), thereby rendering it therapeutically useful in the treatment of a range of proliferative disorders (including but not limited to, cancer, leukaemia, lymphoma, glomerulonephritis, rheumatoid arthritis and psoriasis), immune-mediated and inflammatory disorders, autoimmune and autoimmune-mediated disorders, kidney disorders and viral disorders.

WO 2009/040556 discloses that compound I can be prepared by reacting a compound of formula (II) with 4-(4-methylpiperazin-1-yl)cyclohexanamine in the presence of DIPEA and TBTU in DMF, followed by separation of the trans isomer by preparative RP-HPLC-MS to yield the desired product in a yield of 18%:

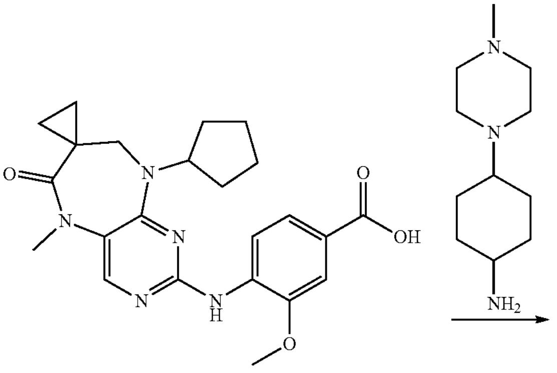

(II)

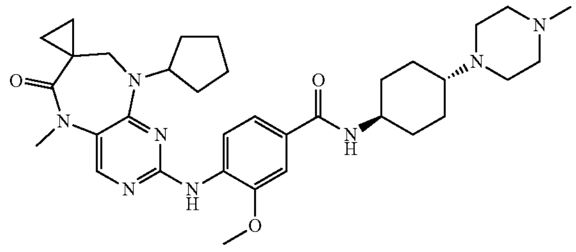

(I)

WO 2009/040556 discloses that 4-(4-methylpiperazin-1-yl)cyclohexanamine, in the form of a mixture of cis/trans isomers, can be prepared by treating N-benzyloxycarbonyl-4-aminocyclohexanone with N-methylpiperazine in the presence of acetic acid and sodium triacetoxyborohydride, followed by hydrogenation.

The present invention seeks to provide an alternative process for preparing compound I, and intermediates for use in said process.

STATEMENT OF INVENTION

A first aspect of the invention relates to a process for preparing a compound of formula (XII), wherein PG is a protecting group, or a compound of formula (XI), comprising the steps of:

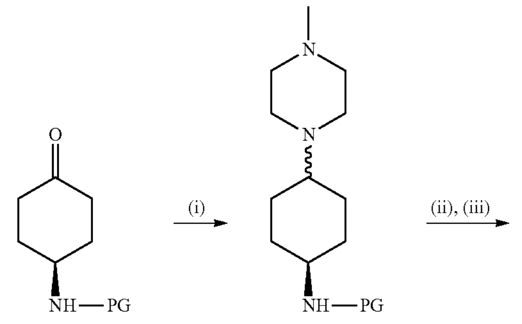

XIII cis/trans-XII

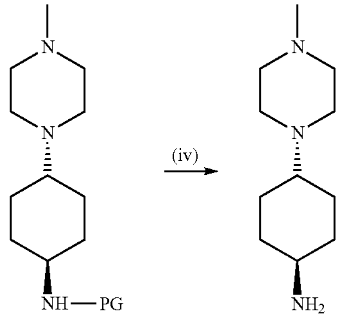

trans-XII XI (i) treating a compound of formula XIII, wherein PG is a protecting group, with N-methylpiperazine to form a compound of formula XII, wherein said compound of formula XII is in the form of a mixture of cis and trans isomers;

(ii) combining the mixture formed in step (i) with an organic solvent and heating the solvent mixture so formed;

(iii) isolating the trans-isomer of the compound of formula XII from the solvent mixture formed in step (ii); and (iv) optionally treating said trans-isomer of the compound of formula XII with an acid to form a compound of formula XI; and isolating said compound of formula XI.

Compound XI is a useful intermediate in the preparation of compound (I). Prior art methods for preparing compound (I) describe the use of a cis/trans mixture of compound XI as an intermediate in the synthesis. Advantageously, isolating the trans-isomer of compound XII (and thus XI) leads to a significant improvement in yield.

A second aspect of the invention relates to a process of preparing a compound of formula I, or a pharmaceutically acceptable salt thereof, which comprises the steps of:

(I) preparing a compound of formula XI by a process as described above in said first aspect;

(II) contacting said compound of formula XI with a compound of formula II to form a compound of formula I;

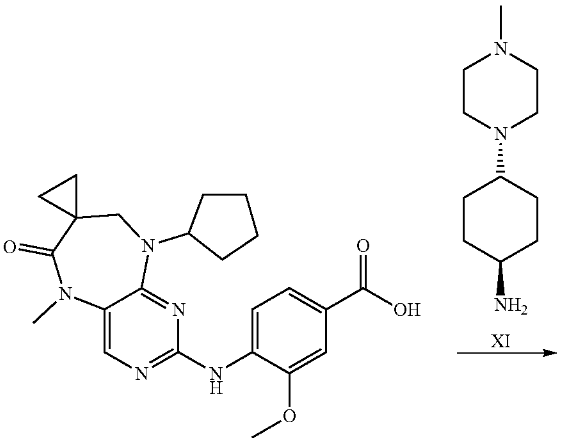

II

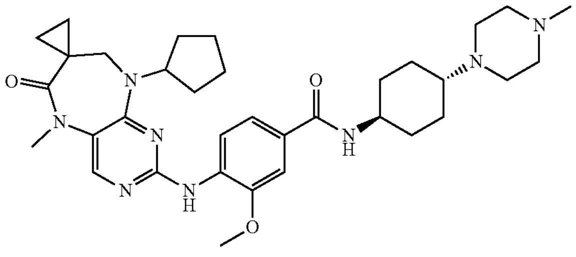

I (III) isolating the compound of formula I; and (IV) optionally converting said compound of formula I to a pharmaceutically acceptable salt form thereof.

A third aspect of the invention relates to a process of preparing a compound of formula I, or a pharmaceutically acceptable salt thereof, which comprises the steps of:

(A) hydrogenating a compound of formula VIII in the presence of Raney nickel catalyst to form a compound of formula VII;

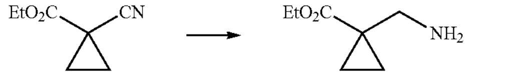

VIII VII (B) contacting said compound of formula VII with cyclopentanone in the presence of a reducing agent, to form a compound of formula VI;

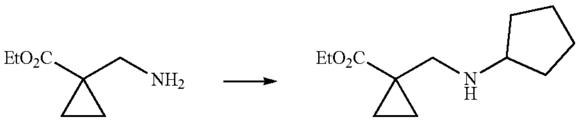

VII VI (C) contacting said compound of formula VI with a compound of formula IX to form a compound of formula V;

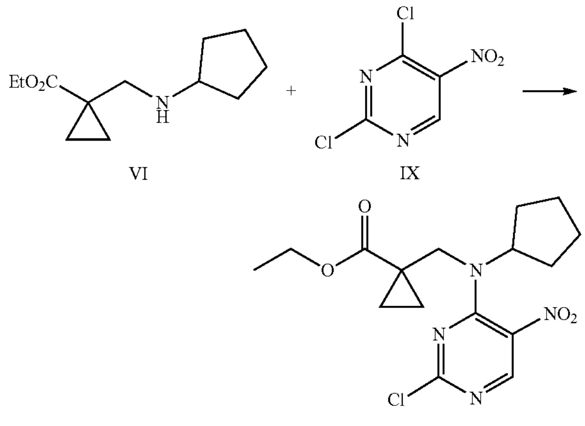

VI IX

V (D) treating said compound of formula V with Fe powder in the presence of acetic acid to form a compound of formula IV;

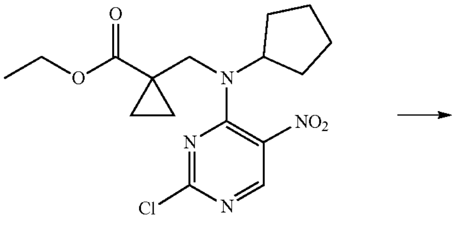

V

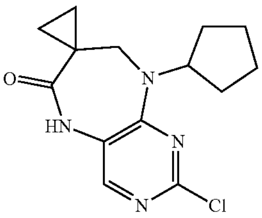

IV (E) treating said compound of formula IV with MeI to form a compound of formula III;

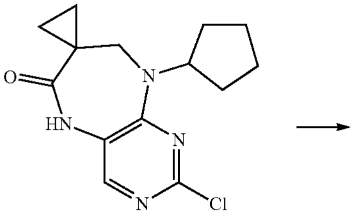

IV

-continued

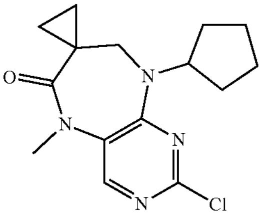

III (F) contacting said compound of formula III with a compound of formula X to form a compound of formula II;

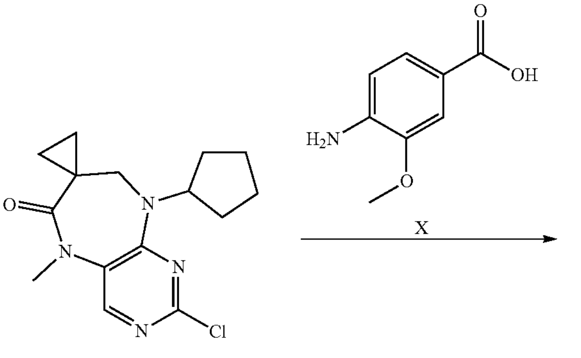

III

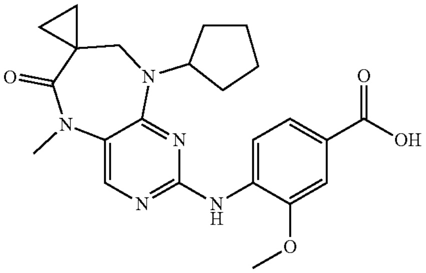

II (G) contacting said compound of formula II with a compound of formula XI to form a compound of formula I, preferably wherein the compound of formula XI is substantially free from the cis-isomer;

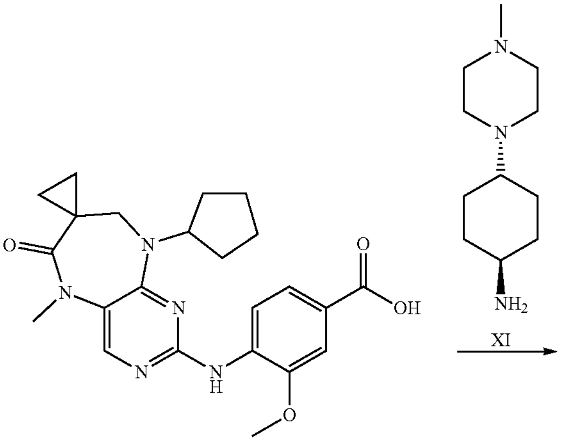

II

-continued

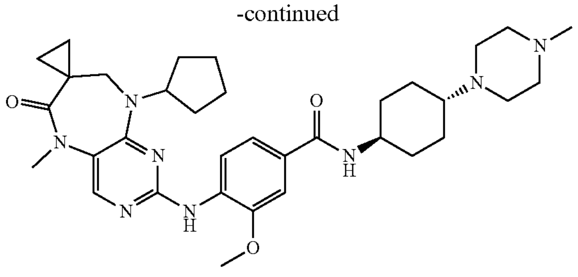

I (H) isolating the compound of formula I; and (I) optionally converting said compound of formula I to a pharmaceutically acceptable salt form thereof.

A fourth aspect of the invention relates to a process for preparing a compound of formula II comprising the steps of contacting a compound of formula III with a compound of formula X in N-methylpyrrolidone, and isolating the compound of formula II:

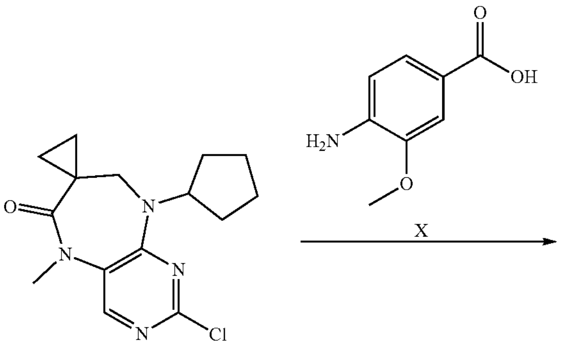

III

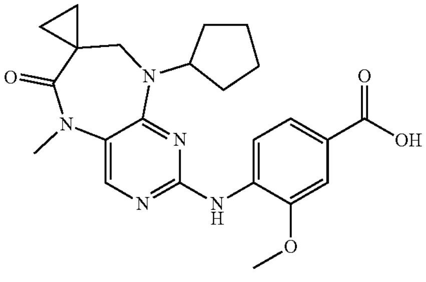

II

A fifth aspect of the invention relates to process of preparing a compound of formula I, or a pharmaceutically acceptable salt thereof, which comprises the steps of:

(I') preparing a compound of formula II by a process as described in the above fourth aspect;

(II') contacting said compound of formula II with a compound of formula XI to form a compound of formula I;

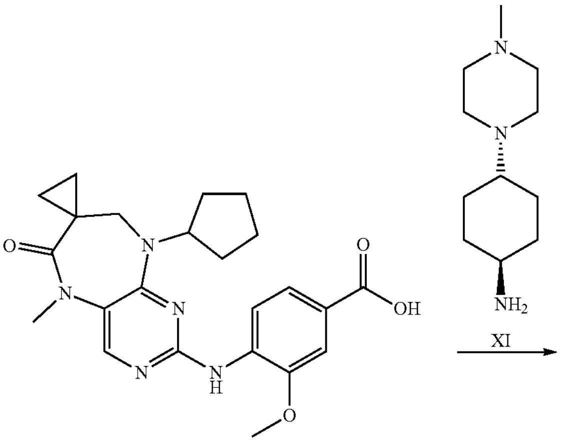

II

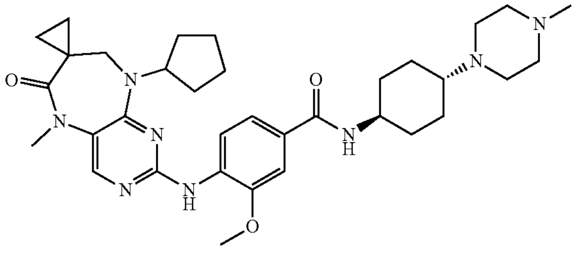

I (III') isolating the compound of formula I; and (IV') optionally converting said compound of formula I to a pharmaceutically acceptable salt form thereof

DETAILED DESCRIPTION

Process for Preparing a Compound of Formula XII or XI

A first aspect of the invention relates to a process for preparing a compound of formula XII, wherein PG is a protecting group, said process comprising the steps of:

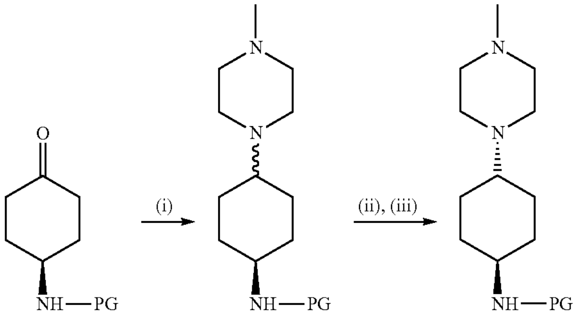

XIII cis/trans-XII trans-XII (i) treating a compound of formula XIII, wherein PG is a protecting group, with N-methylpiperazine to form a compound of formula XII, wherein said compound of formula XII is in the form of a mixture of cis and trans isomers;

(ii) combining the mixture formed in step (i) with an organic solvent and heating the solvent mixture so formed; and (iii) isolating the trans-isomer of the compound of formula XII from the solvent mixture formed in step (ii).

In one embodiment, the process further comprises the step of converting said compound of formula trans-XII to a compound of formula XI, by treating said compound of formula trans-XII with an acid and isolating said compound of formula XI.

As used herein, "PG" refers to an amino protecting group. The skilled person will be familiar with suitable amino protecting groups. Examples of amino protecting groups can be found in Green et al, "Protective Groups in Organic Chemistry", (Wiley, 2nd ed. 1991) and Harrison et al, "Compendium of Synthetic Organic Methods", Vols. 1-8 (John Wiley and Sons, 1971-1996). Representative amino protecting groups include, but are not limited to, formyl, acetyl (Ac), trifluoroacetyl, benzyl (Bn), dibenzyl ($Bn_2$), methyl carbamate, formamide, benzyloxycarbonyl (CBZ), tert-butoxycarbonyl (BOC), trimethylsilyl (TMS), 2-trimethylsilyethanesulfonyl, (SES), trityl and substituted trityl groups, allyloxycarbonyl, 9-fluorenylmethyloxycarbonyl (FMOC), nitroveratryloxycarbonyl (NVOC) and the like.

Studies by the Applicant have demonstrated that the nature of the protecting group, PG, in combination with the choice of reducing agent can influence the ratio of trans to cis isomer formed in step (i) of the process according to the first aspect of the invention. In this respect, certain protecting groups lead to a preference for the formation of the trans isomer relative to the cis isomer. Without wishing to be bound by theory, it is believed that mixtures containing a greater proportion of trans to cis isomer are generally easier to manipulate and purify, and that in some cases the desired trans isomer can be obtained without the need for chromatography. This has obvious benefits in terms of scale-up.

Preferably, the ratio of trans to cis isomer is at least about 60 to about 40 (by weight percent), more preferably, at least about 65 to about 35, even more preferably at least about 70 to about 30, more preferably still, at least about 75 to about 25, more preferably at least about 80 to about 20, more preferably at least about 85 to about 15, even more preferably at least about 90 to about 10.

Preferably, the mixture formed in step (i) of the process comprises a proportion of at least 60% of the trans isomer, more preferably at least about 65%, even more preferably at least about 70%, more preferably still, at least about 75%, more preferably at least about 80%, more preferably at least about 85%, even more preferably at least about 90% of the trans isomer relative to the cis isomer.

Preferably, the ratio of trans to cis isomer is at least 60% (by weight) in favour of the trans isomer, more preferably at least about 65%, even more preferably at least about 70%, more preferably still, at least about 75%, more preferably at least about 80%, more preferably at least about 85%, even more preferably at least about 90% in favour of the trans isomer relative to the cis isomer.

In one preferred embodiment, the ratio of trans to cis isomer is about 60 to about 40 (by weight percent), more preferably, about 65 to about 35, even more preferably about 70 to about 30, more preferably still, about 75 to about 25, more preferably about 80 to about 20, more preferably about 85 to about 15, even more preferably about 90 to about 10.

In one particularly preferred embodiment, PG is an acetyl group. By way of illustration, studies by the Applicant have demonstrated that the use of an acetyl protecting group leads to a particularly favourable ratio of trans-XII to cis-XII in step (i), for example, a ratio of trans-XII to cis-XII of about 65:35% in terms of the crude material so produced. The trans-isomer (trans-XII) can then be separated from the crude mixture and further purified. The acetyl group can then be removed and compound XI further purified by conventional means.

In another particularly preferred embodiment, PG is tert-butoxycarbonyl (BOC). By way of example, studies by the Applicant have demonstrated that the use of a BOC protecting group leads to an even more favourable ratio of trans/cis isomer, for example, a ratio of trans-XII to cis-XII of about 75:25% in terms of the crude material so produced. The trans-isomer (trans-XII), can then be separated from the crude mixture and further purified. The use of a BOC protecting group also leads to an improved yield of trans-XII (~32%) compared to an acetyl protecting group (~25%). The BOC group can then be removed and compound XI further purified by conventional means. Advantageously, the BOC-protected derivative XII is crystalline and thus easy to manipulate and purify in the laboratory (for example, by avoiding the need for chromatography). This is an important factor in yield optimisation and scale up. Furthermore, the BOC protecting group can be removed under mild conditions, which again is an important factor for the development of scale up procedures.

In another preferred embodiment, PG is dibenzyl ($Bn_2$).

In one preferred embodiment, step (i) comprises the step of (a) forming a mixture comprising a compound of formula XIII, N-methylpiperazine, a solvent and an acid, and heating said mixture.

In one preferred embodiment, step (i) further comprises the step of (b) cooling the mixture obtained in step (a), and diluting with a solvent.

In one preferred embodiment, step (i) further comprises the step of (c) treating the mixture obtained in step (b) with a reducing agent.

In one preferred embodiment, step (i) further comprises the step of (d) isolating the compound of formula XII as a mixture of cis and trans isomers.

In one preferred embodiment, step (i) comprises the steps of:

(a) forming a mixture comprising a compound of formula XIII, N-methylpiperazine, a solvent and an acid, and heating said mixture;
(b) cooling the mixture obtained in step (a), and diluting with a solvent; and
(c) treating the mixture obtained in step (b) with a reducing agent; and
(d) isolating the compound of formula XII as a mixture of cis and trans isomers.

In one preferred embodiment, the reaction mixture in step (i)(a) is heated to a temperature of at least 60° C., even more preferably at least 70° C., more preferably at least 80° C., even more preferably at least 90° C.

Preferably, the reaction mixture in step (i)(a) is subjected to azeotropic distillation. More preferably, the azeotropic distillation is carried out using a Dean and Stark apparatus.

A Dean and Stark apparatus is typically used in azeotropic distillations, for example for the removal of water generated during a reaction. When using a Dean and Stark apparatus, the reaction is performed in a solvent that is immiscible with water; which forms a lower-boiling azeotrope with water; and which has a density less than water. Under refluxing conditions, a Dean and Stark apparatus allows the solvent to be continuously returned to the reaction mixture, whereas the water is collected in the Dean and Stark apparatus to be subsequently drained off. Examples of suitable solvents for the extraction of water from reactions using a Dean and Stark apparatus include toluene, benzene, and xylene.

In one preferred embodiment, the solvent in step (i)(a) is immiscible with water.

In one preferred embodiment, the solvent in step (i)(a) forms a lower-boiling azeotrope with water.

In one preferred embodiment, the solvent in step (i)(a) has a density less than water.

In one preferred embodiment, the solvent in step (i)(a) is immiscible with water, forms a lower-boiling azeotrope with water, and has a density less than water.

In one preferred embodiment, the solvent in step (i)(a) is selected from toluene, benzene, and xylene.

In one preferred embodiment, the solvent in step (i)(a) is toluene.

In one preferred embodiment, the acid is a sulfonic acid, more preferably selected from benzene sulfonic acid, para-toluene sulfonic acid and methanesulfonic acid. In one particularly preferred embodiment, the acid is methanesulfonic acid.

In one highly preferred embodiment, the solvent in step (i) is toluene and the acid is methanesulfonic acid.

In one preferred embodiment, step (i)(a) comprises heating the mixture to reflux.

Preferably, the mixture is heated at reflux temperature for a period of at least 2 hours, more preferably at least 3 hours, more preferably at least 4 hours, even more preferably at least 5 hours. Preferably, the reaction is carried out in a Dean and Stark apparatus.

In one preferred embodiment, step (i)(b) comprises cooling the mixture to a temperature of about 50° C. to about 60° C., more preferably, about 50° C. to about 55° C., even more preferably, about 50° C.

As used throughout, the term "cooling" refers to reducing the temperature, for example, of a reaction mixture. The term includes active methods (e.g. subjecting the reaction mixture to cooling conditions such as immersing the reaction vessel in a cooling bath), and passive methods e.g. allowing the reaction mixture to cool (for example, to room temperature) by removing the heat source.

In one preferred embodiment, step (i)(b) comprises diluting the mixture with an alcohol, more preferably, an alkyl alcohol, more preferably ethanol or methanol, even more preferably, ethanol.

In one preferred embodiment, step (i)(c) comprises treating the mixture formed in step (i)(b) (which comprises an intermediate enamine species) with a reducing agent:

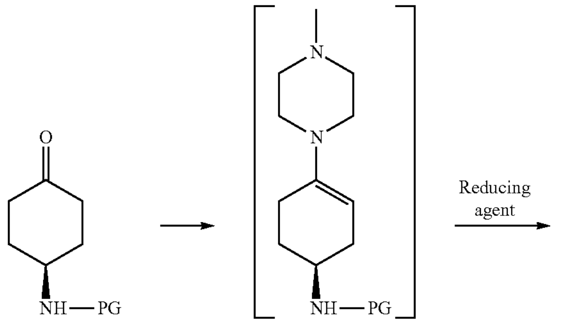

XIII

Intermediate enamine

-continued

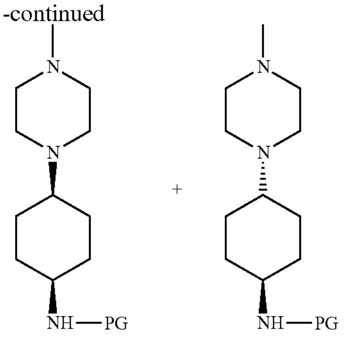

cis-XII trans-XII

Preferably, the reducing agent is a borohydride reducing agent, more preferably, $NaBH_4$ or $LiBH_4$.

In one particularly preferred embodiment, the reducing agent is $NaBH_4$.

In another particularly preferred embodiment, the reducing agent is $LiBH_4$.

The skilled person would understand that other reducing agents would also be suitable for use in step (i)(c), including but not limited to picoline-borane, borazane and sodium triacetoxyborohydride (STAB).

In one preferred embodiment, step (i)(c) comprises treating the mixture formed in step (i)(b) (which comprises the intermediate enamine species) with a reducing agent, for example, $NaBH_4$ or $LiBH_4$, wherein the reducing agent is added at a temperature of about 10° C. to about 25° C., more preferably, about 15° C. to about 20° C. Preferably, the resulting mixture is stirred for at least 2 hours, more preferably at least 3 hours, more preferably at least 4 hours, even more preferably at least 5 hours, even more preferably, overnight. The reducing agent (e.g. $NaBH_4$ or $LiBH_4$) is then decomposed by treating with acid, preferably HCl, preferably at a temperature of about 10° C. to about 20° C., more preferably, about 10° C. to about 15° C. The aqueous layer is then treated with a base (e.g. $K_2CO_3$), the solids filtered off and washed with an organic solvent (e.g. dichloromethane). The filtrate is then concentrated and extracted with an organic solvent (e.g. dichloromethane), basified to a pH of approximately 10 (preferably with KOH), and further extracted with an organic solvent (e.g. dichloromethane). The combined organic layers are then dried and concentrated. The crude product may be purified by column chromatography, for example, using basic alumina, to give a solid corresponding to compound XII which contains a mixture of cis- and trans-isomers.

The process of the invention further comprises isolating the trans-isomer of compound XII from the mixture of cis- and trans-isomers. The Applicant has demonstrated that this can be achieved by precipitating the trans-isomer of compound XII from a solvent mixture containing the cis- and trans-isomers. Thus, the invention further comprises the steps of:

(ii) combining the mixture formed in step (i) with an organic solvent and heating the solvent mixture so formed; and (iii) isolating the trans-isomer of the compound of formula XII from the solvent mixture formed in step (ii).

In one preferred embodiment, the organic solvent in step (ii) is acetonitrile.

In one preferred embodiment, step (ii) comprises heating the solvent mixture to dissolve the mixture of cis- and trans-isomers. Preferably, the mixture is heated to a temperature of at least 40° C., even more preferably, at least 50° C., even more preferably at least 60° C., even more preferably at least 70° C., more preferably at least 80° C. In one preferred embodiment, the mixture is heated to reflux temperature. Preferably, the mixture is heated to reflux temperature for a period of at least 5 minutes, more preferably at least 10 minutes, even more preferably at least 15 minutes. On cooling, the trans-isomer precipitates out of solution and can be isolated by filtration (step (iii)). Preferably, the trans-isomer of compound XII is in crystalline form.

Thus, in one preferred embodiment, step (iii) comprises cooling the mixture such that the trans-isomer of formula XII precipitates out of solution, filtering the precipitate so formed, and optionally washing and/or drying the precipitate.

In one preferred embodiment, the precipitate comprises less than about 5% of the cis-isomer, more preferably, less than about 2%, even more preferably less than about 1%, more preferably still less than about 0.5% or 0.1% of the cis-isomer.

Preferably, the precipitate comprises ≥95% of the trans-isomer, more preferably, ≥98%, even more preferably ≥99%, more preferably still ≥99.5% or ≥99.9% of the trans-isomer.

In one preferred embodiment, the trans-isomer of compound XII is substantially free from the cis-isomer. As used herein, “substantially free from the cis-isomer” means that the cis-isomer is present in such a level that it is undetectable by $^{1}H$ NMR spectroscopy.

In one preferred embodiment, step (iii) comprises cooling the mixture to a temperature of about 0 to about 15° C., more preferably, about 5 to about 10° C.

In one preferred embodiment, the process of the invention further comprises the step of removing the protecting group PG from compound XII to form a compound XI. The skilled person would be familiar with the conditions required for removal of the protecting group. In one preferred embodiment, the process comprises treating said compound of formula XII with an acid to form a compound of formula XI (step (iv)). Preferably the acid is a strong acid.

In one preferred embodiment, the process of the invention comprises treating the compound of formula XII with concentrated HCl to remove the protecting group PG. The skilled person would understand that other acids (e.g. trifluoroacetic acid) would also be suitable and that the choice of acid may depend on the nature of the protecting group. Preferably, the reaction mixture is heated to a temperature of at least 100° C., more preferably, at least 105° C., preferably for a period of at least 1 hour. More preferably, the reaction mixture is then heated at a temperature of about 95° C. to about 105° C. for at least 10 hours, more preferably at least 12 hours, even more preferably at least 15 hours. Preferably, the reaction mixture is then cooled to a temperature of about 15° C. to about 25° C. before the portionwise addition of potassium hydroxide to give a final pH of about 12. The compound of formula XI can then be isolated by conventional methods to yield a low melting solid which was shown to be the trans-isomer by HRGC.

Process for Preparing a Compound of Formula II

Another aspect of the invention relates to a process for preparing a compound of formula II comprising the steps of contacting a compound of formula III with a compound of formula X in N-methylpyrrolidone, and isolating the compound of formula II:

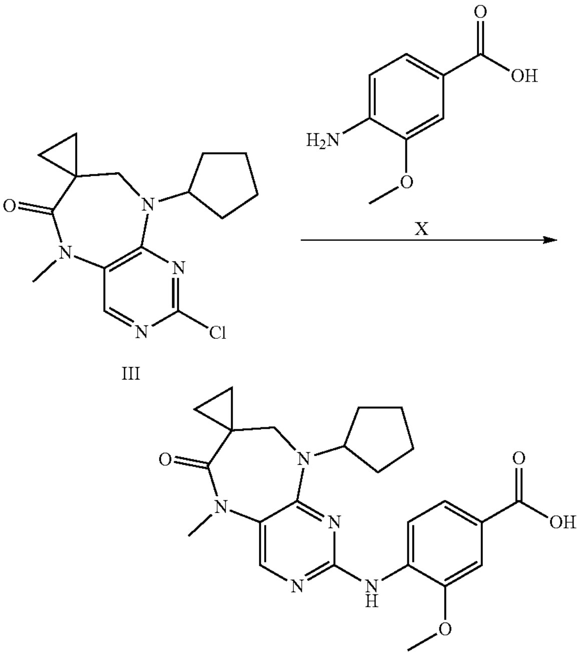

II

Advantageously, the use of N-methylpyrrolidone as the solvent in this step significantly increases the yield. For example, the reaction proceeds in a yield of 91% when carried out in N-methylpyrrolidone, compared to 74% when carried out in a mixture of trifluoroacetic acid and 2,2,2-trifluoroethanol (see WO 2009/040556).

Preferably, the reaction mixture is heated to a temperature of at least 110° C., more preferably, to about 115° C. to about 125° C. Preferably, the mixture is heated for a period of at least 24 hours, more preferably, at least 36 hours. Compound II can be isolated and purified using conventional methods.

Process for Preparing a Compound of Formula I

Another aspect of the invention relates to a process for preparing a compound of formula I, or a pharmaceutically acceptable salt thereof, which comprises the steps of:

(I) preparing a compound of formula XI by a process as described above in the first aspect of the invention;

(II) contacting said compound of formula XI with a compound of formula II to form a compound of formula I;

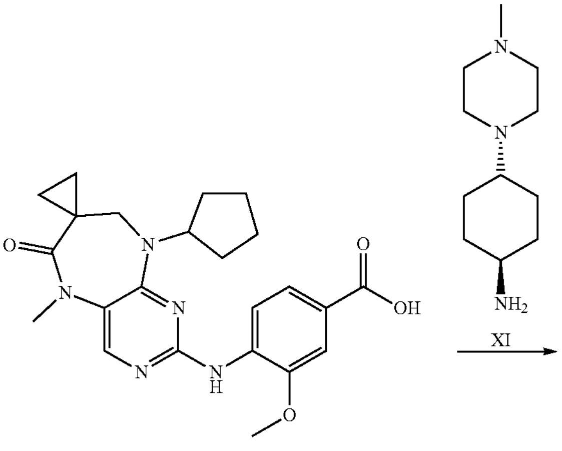

II

-continued

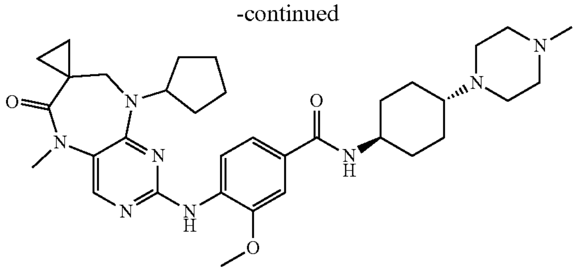

I (II) isolating the compound of formula I; and (IV) optionally converting said compound of formula I to a pharmaceutically acceptable salt form thereof.

In one preferred embodiment, the compound of formula XI comprises less than about 5% of the cis-isomer, more preferably, less than about 2%, even more preferably less than about 1%, more preferably still less than about 0.5% or 0.1% of the cis-isomer.

Preferably, the compound of formula XI comprises ≥95% of the trans-isomer, more preferably, ≥98%, even more preferably ≥99%, more preferably still ≥99.5% or ≥99.9% of the trans-isomer.

In one preferred embodiment, the compound of formula XI is substantially free from the cis-isomer.

Advantageously, the Applicant has shown that using trans-compound XI (rather than a mixture of cis/trans-compound XI) in the transformation of compound II to compound I leads to a dramatic improvement in yield (86% using trans-compound XI compared to 18% using a mixture of cis/trans-compound XI as described in WO 2009/040556).

In one preferred embodiment, step (II) is carried out in the presence of an organic solvent, a base and a coupling reagent. Suitable solvents will be familiar to the skilled person and include, for example, dichloromethane and dimethyl formamide. Suitable coupling reagents will be familiar to the skilled person and include, for example, (2-(1H-benzotriazol-1-yl)-1,1,3,3-tetramethyl-uronium hexafluorophosphate (HBTU) and 2-(1H-benzotriazol-1-yl)-1,1,3,3-tetramethyluronium tetrafluoroborate (TBTU). Suitable bases will be familiar to the skilled person and include, for example, tertiary aliphatic amine bases. More preferably, the base is selected from N,N-diisopropylethylamine (DIPEA), tri-$^{N}$propylamine, and tri-$^{N}$butylamine. More preferably still, the base is N,N-diisopropylethylamine (DIPEA).

In one preferred embodiment, step (II) is carried out in the presence of dichloromethane, N,N-diisopropylethylamine (DIPEA) and (2-(1H-benzotriazol-1-yl)-1,1,3,3-tetramethyl-uronium hexafluorophosphate (HBTU).

In another preferred embodiment, step (II) is carried out in the presence of DMF, N,N-diisopropylethylamine (DIPEA) and 2-(1H-benzotriazol-1-yl)-1,1,3,3-tetramethyl-uronium tetrafluoroborate (TBTU).

Preferably, step (II) comprises suspending the compound of formula II in the organic solvent and adding the coupling reagent thereto at a temperature of from about 15° C. to about 25° C. The base is then added, keeping the mixture within the same temperature range. Compound XI is then added to the mixture keeping the mixture within the same temperature range. The product, compound I, can be isolated using conventional methods.

More preferably, step (II) comprises suspending the compound of formula II in dichloromethane and adding HBTU thereto at a temperature of from about 15° C. to about 25° C. DIPEA is then added, keeping the mixture within the same temperature range. Compound XI is then added to the mixture keeping the mixture within the same temperature range. The product, compound I, can be isolated using conventional methods.

In one preferred embodiment, the process further comprises the step of preparing a compound of formula II by contacting a compound of formula III with a compound of formula X:

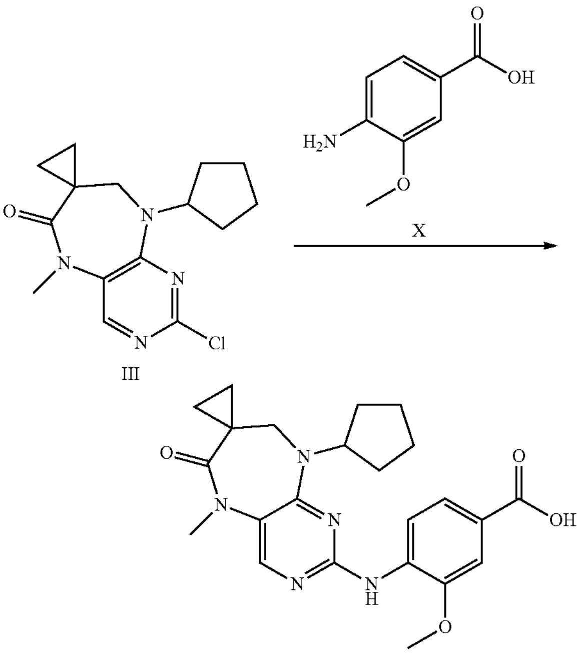

X

III

II

In one preferred embodiment, the reaction converting compound III into compound II is carried out in N-methylpyrrolidone. Preferably, the reaction mixture is heated to a temperature of at least 110° C., more preferably, to about 115° C. to about 125° C. Preferably, the mixture is heated for a period of at least 24 hours, more preferably, at least 36 hours. Compound II can be isolated and purified using conventional methods.

In an alternative preferred embodiment, the reaction converting compound III into compound II is carried out in the presence of trifluoroacetic acid (TFA) and 2,2,2-trifluoroethanol (TFE). Preferably, the reaction is carried out in the presence of 5 equivalents of TFA relative to the compound of formula III.

In one preferred embodiment, the process of the invention further comprises the step of preparing a compound of formula III by treating a compound of formula IV with MeI:

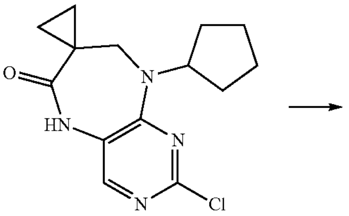

IV

-continued

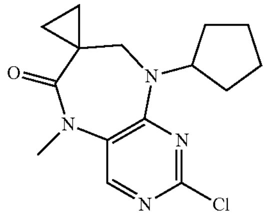

III

Preferably, the reaction is carried out in an organic solvent, more preferably THF. The skill person would appreciate that other solvents would also be suitable.

In one preferred embodiment, the conversion of compound IV into compound III is carried out in the presence of THF and t-BuOK. Preferably, the reaction is carried out at a temperature of less than about 10° C., more preferably, at a temperature of from about 0 to about 5° C. Preferably, the compound of formula IV is added portionwise to a suspension of t-BuOK in THF followed by the addition of Mel thereto. Preferably, the resulting reaction mixture is stirred at a temperature of about 0 to about 5° C. for at least 15 minutes and then warmed to a temperature of about 20° C. to about 25° C. Preferably, the mixture is then stirred a temperature of about 20° C. to about 25° C. for at least 6 hours, more preferably at least 12 hours. Compound III can be isolated and purified using conventional methods.

In an alternative preferred embodiment, the conversion of compound IV into compound III is carried out using Mel and NaH in DMF. The skilled person would appreciate that other conditions and/or reagents for the alkylation step could also be used.

In one preferred embodiment, the process of the invention further comprises the step of preparing a compound of formula IV by treating a compound of formula V with Fe powder in the presence of acetic acid:

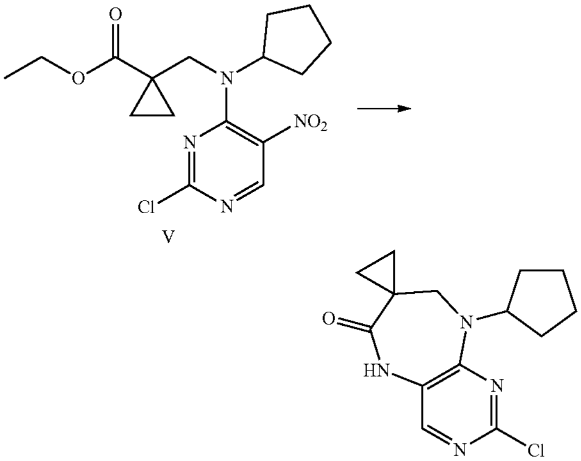

V

IV

In one preferred embodiment, the conversion of compound V to compound IV is carried out at a temperature of from about 25 to about 30° C.

Preferably, the acetic acid is heated to at least 50° C., more preferably at least 60° C. and Fe powder is added thereto. The mixture is then cooled to about 25° C. and compound V added thereto. Preferably, the resulting mixture is stirred for a period of at least 6 hours, more preferably at least 12 hours, at about 25° C. Compound IV can be isolated and purified using conventional methods.

In one preferred embodiment, the process of the invention further comprises the step of preparing a compound of formula V by contacting a compound of formula VI with a compound of formula IX:

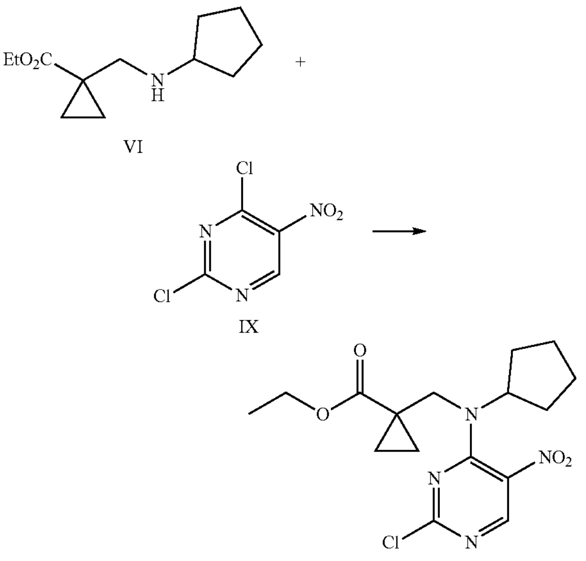

VI

IX

V

In one preferred embodiment, the reaction to convert compound VI and IX to compound V is carried out in the presence of a solvent and a base.

In one preferred embodiment, the reaction to convert compound VI and IX to compound V is carried out in the presence of acetone and $K_2CO_3$. Preferably, the reaction is carried out at a temperature of below about 10° C., more preferably, below about 5° C.

Preferably, a solution of compound IX in acetone is cooled to a temperature of from about 0° C. to about 5° C. and $K_2CO_3$ added thereto. A solution of compound VI in acetone is then added to the mixture. Compound V can be isolated and purified using conventional methods.

In one preferred embodiment, the process of the invention further comprises the step of preparing a compound of formula VI by contacting a compound of formula VII with cyclopentanone in the presence of a reducing agent (i.e. in a reductive amination reaction):

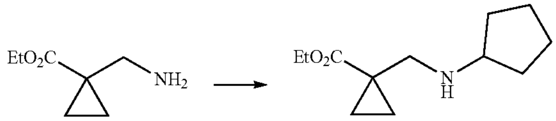

VII

VI

Preferably, the reaction is carried out in an organic solvent, more preferably, dichloromethane. The skilled person would appreciate that other organic solvents would also be suitable. Preferably, the reducing agent is sodium triacetoxyborohydride (STAB), although the skilled person will understand that other reducing agents would also be suitable. In one preferred embodiment, the reaction to convert compound VII to compound VI is carried out in the presence of sodium triacetoxyborohydride (STAB) and dichloromethane. Preferably, the reaction is carried out at room temperature. Preferably, the reaction mixture is stirred for a period of at least 6 hours, more preferably at least 12 hours, at about 25° C. Compound VI can be isolated and purified using conventional methods.

In one preferred embodiment, the process of the invention further comprises the step of preparing a compound of formula VII by hydrogenating a compound of formula VIII, preferably in the presence of a solvent and Raney nickel catalyst:

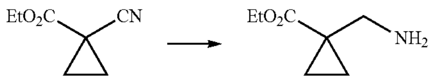

VIII VII

Preferably, the solvent for the hydrogenation reaction is ethanol. The skilled person would appreciate that other solvents and/or reaction conditions for the hydrogenation step would also be suitable In one preferred embodiment, the process comprises the step of converting the compound of formula I to a pharmaceutically acceptable salt form thereof. Pharmaceutically acceptable salts of the compound of formula I can be obtained using routine methods that will be familiar to the skilled person in the art.

As used herein, the term pharmaceutically acceptable salt includes suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$-alkyl- or aryl-sulfonic acids which are unsubstituted or substituted (for example, by a halogen) such as methane- or p-toluene sulfonic acid. Preferably, the pharmaceutically acceptable salt is an HCl salt.

Thus, in one preferred embodiment, the invention further comprises the step of treating a compound of formula (I) with a suitable acid as described above and isolating the resulting pharmaceutically acceptable salt. Preferably, the reaction takes place in the presence of a suitable solvent, for example, ethanol or a mixture of ethanol/THF. Preferably, the pharmaceutically acceptable salt is isolated by filtration and dried in vacuo.

Another aspect of the invention relates to a process of preparing a compound of formula I, or a pharmaceutically acceptable salt thereof, which comprises the steps of:

(I') preparing a compound of formula II by contacting a compound of formula III with a compound of formula X in N-methylpyrrolidone, and isolating the compound of formula II;

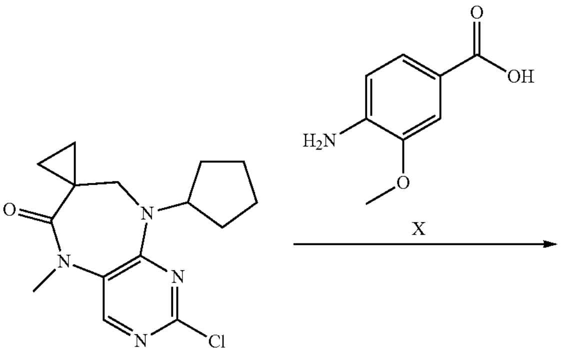

X

III

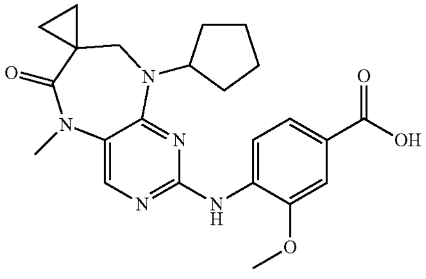

II (II') contacting said compound of formula II with a compound of formula XI to form a compound of formula I;

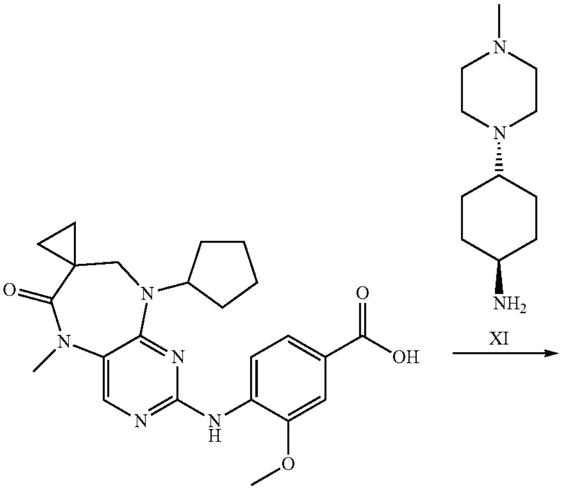

XI

II

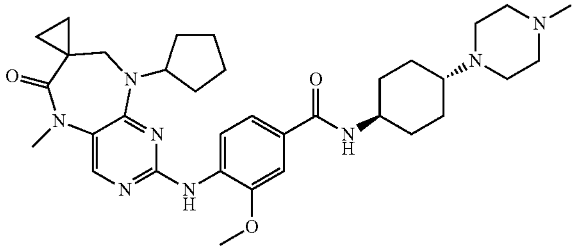

I (III') isolating the compound of formula I; and (IV') optionally converting said compound of formula I to a pharmaceutically acceptable salt form thereof In one preferred embodiment, the compound of formula XI comprises less than about 5% of the cis-isomer, more preferably, less than about 2%, even more preferably less than about 1%, more preferably still less than about 0.5% or 0.1% of the cis-isomer.

Preferably, the compound of formula XI comprises ≥95% of the trans-isomer, more preferably, ≥98%, even more preferably ≥99%, more preferably still ≥99.5% or ≥99.9% of the trans-isomer.

In one preferred embodiment, the compound of formula XI is substantially free from the cis-isomer.

Another aspect of the invention relates to a process of preparing a compound of formula I, or a pharmaceutically acceptable salt thereof, which comprises the steps of:

(A) hydrogenating a compound of formula VIII in the presence of Raney nickel catalyst to form a compound of formula VII;

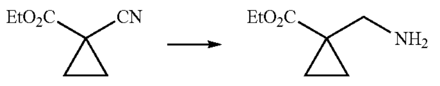

VIII VII (B) contacting said compound of formula VII with cyclopentanone in the presence of a reducing agent to form a compound of formula VI;

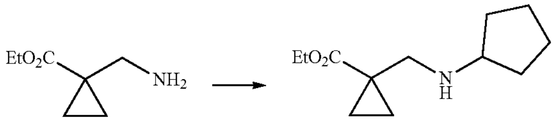

VII VI (C) contacting said compound of formula VI with a compound of formula IX to form a compound of formula V;

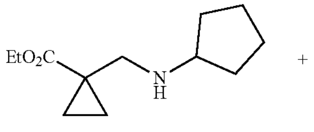

VI

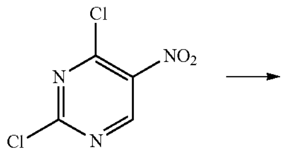

IX

-continued

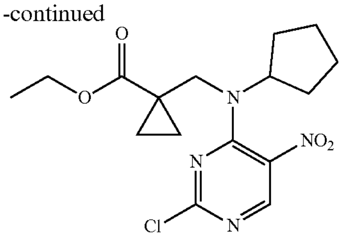

V (D) treating said compound of formula V with Fe powder in the presence of acetic acid to form a compound of formula IV;

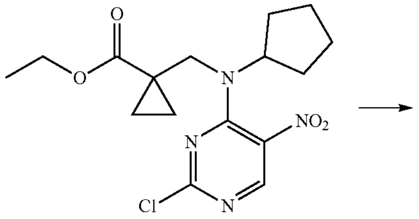

V

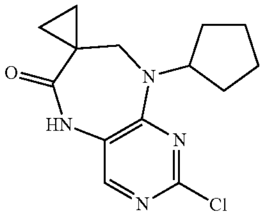

IV (E) treating said compound of formula IV with MeI to form a compound of formula III;

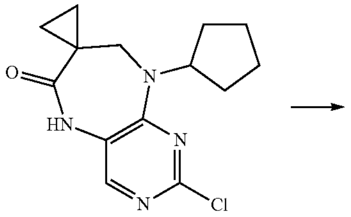

IV

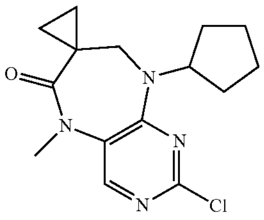

III (F) contacting said compound of formula III with a compound of formula X to form a compound of formula II;

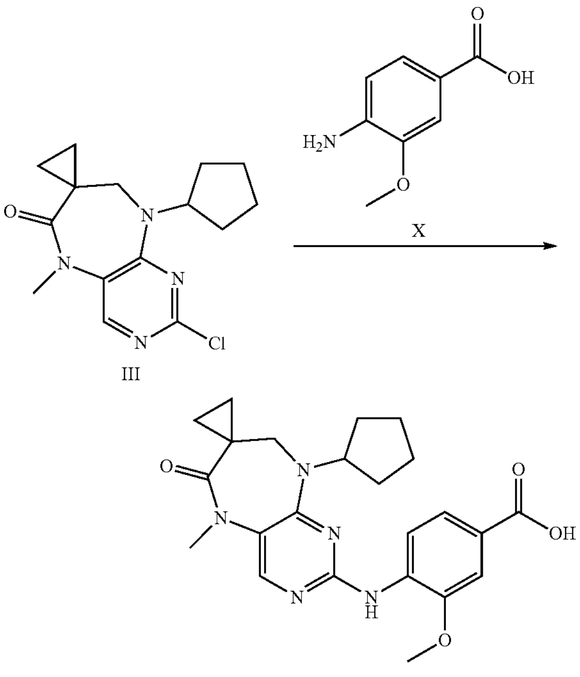
III
X
II (G) contacting said compound of formula II with a compound of formula XI to form a compound of formula I;

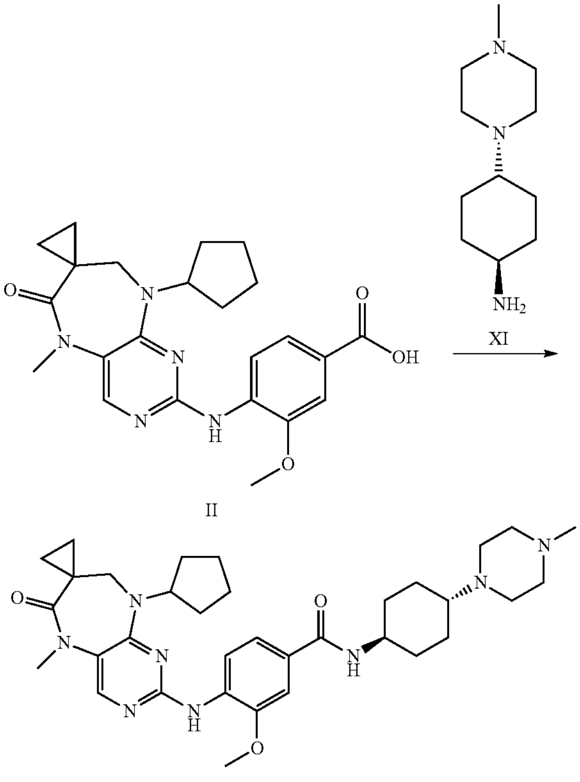
XI
II
I (H) isolating the compound of formula I; and (I) optionally converting said compound of formula I to a pharmaceutically acceptable salt form thereof.

In one preferred embodiment, the compound of formula XI in step (G) comprises less than about 5% of the cis-isomer, more preferably, less than about 2%, even more preferably less than about 1%, more preferably still less than about 0.5% or 0.1% of the cis-isomer.

Preferably, the compound of formula XI in step (G) comprises ≥95% of the trans-isomer, more preferably, ≥98%, even more preferably ≥99%, more preferably still ≥99.5% or ≥99.9% of the trans-isomer.

Preferably the compound of formula XI in step (G) is substantially free from the cis-isomer.

Preferred embodiments for steps (A)-(I) of the third aspect are as described above for the second aspect of the invention.

The present invention is further described by way of the following non-limiting examples.

EXAMPLES

Abbreviations

EtOH ethanol
MeOH methanol
EtOAc ethyl acetate
DCM dichloromethane
DMF dimethyl formamide
RT room temperature
$Et_2O$ diethyl ether
Mel methyl iodide
t-BuOK potassium tert-butoxide
NMP N-methylpyrrolidone
HPLC high performance liquid chromatography
HBTU (2-(1H-benzotriazol-1-yl)-1,1,3,3-tetramethyluronium hexafluorophosphate
TBTU 2-(1H-benzotriazol-1-yl)-1,1,3,3-tetramethyluronium tetrafluoroborate
DIPEA N,N-diisopropylethylamine
HOBt hydroxybenzotriazole
HRGC high resolution gas chromatography
KF Karl Fischer
MeCN acetonitrile

Instruments and Methods

Solution Proton NMR $^1H$ NMR spectra were collected using a JEOL EX 270 MHz spectrometer equipped with an auto-sampler. The samples were dissolved in a suitable deuterated solvent for analysis. The data was acquired using Delta NMR Processing and Control Software version 4.3.

High Resolution Gas Chromatography (HRGC)

HRGC spectra were obtained by Agilent 6890 series gas chromatography fitted with a headspace sampler. The samples were dissolved in methanol.

Example 1

Preparation of Compound (I)

Compound (I) in free base form can be prepared in accordance with the synthesis shown below in Schemes 1, 2 and 3:

Scheme 1: Synthesis of Compound III
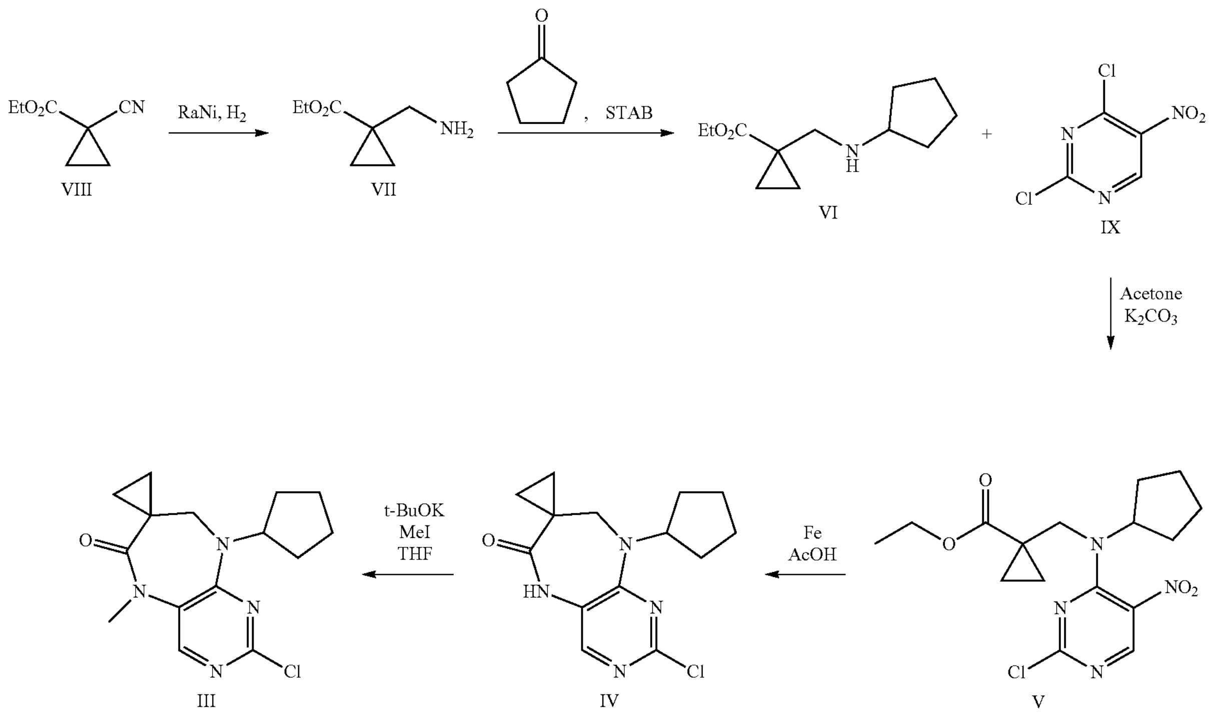
VIII, VII, VI, IX, V, IV, III
Scheme 2: Synthesis of Compound XI
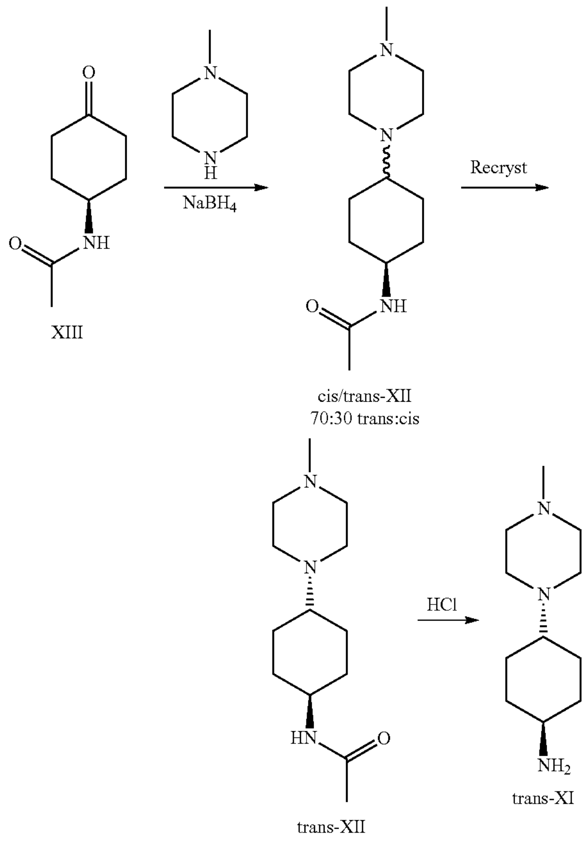
XIII, cis/trans-XII, 70:30 trans:cis, trans-XII, trans-XI Scheme 3: Final stages

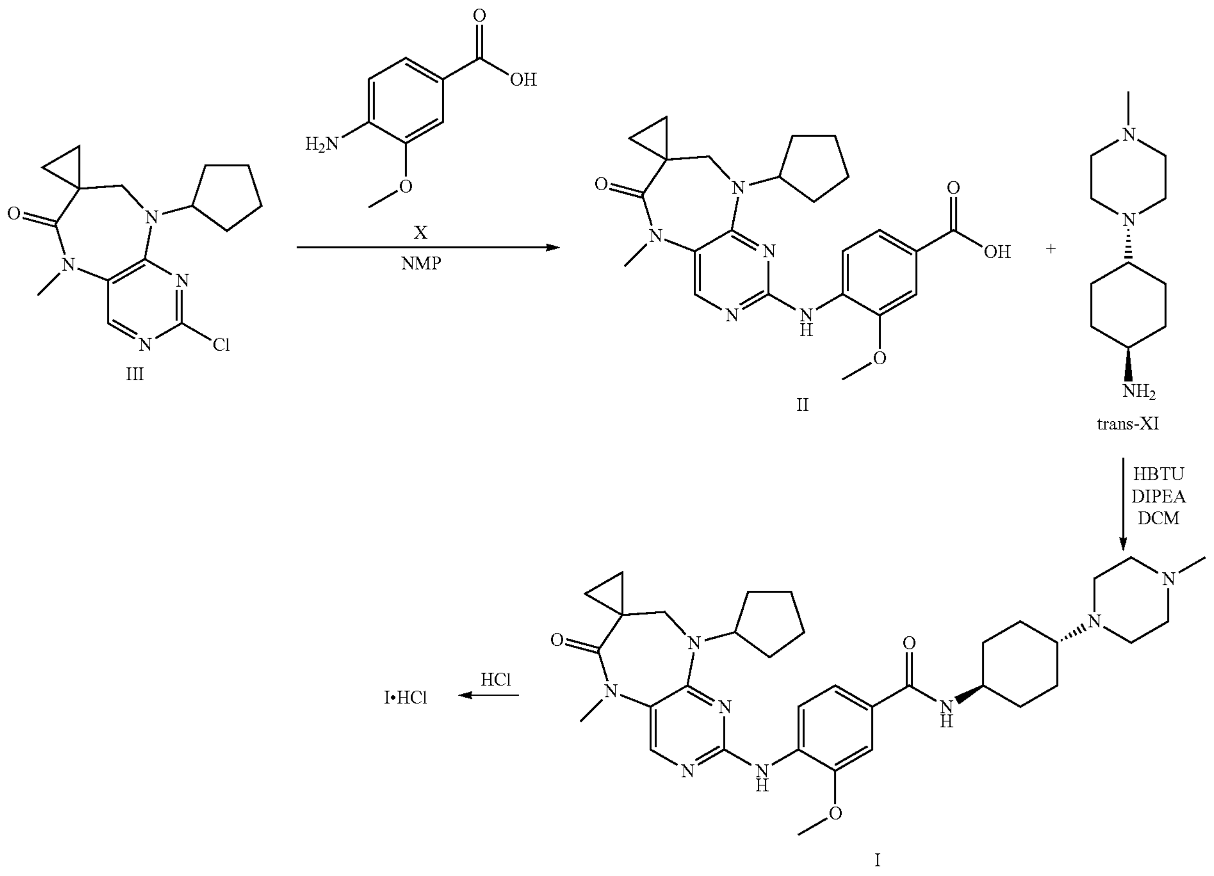

Example 1: Synthesis of Compound (I)

1.1 Synthesis of Compound (III)

(i) Compound VII

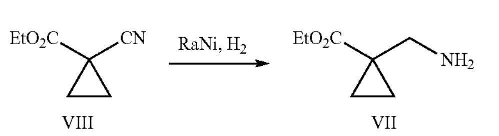

Raney Nickel catalyst (200 g, 50% water) was washed with EtOH (3×100 ml, solvent was decanted). The catalyst was then suspended in ethanol (200 ml). To a suspension of Raney Nickel (200 g, 50% suspension in EtOH) in EtOH (3 L) was added ethyl-1-cyanocyclopropanecarboxylate VIII (600 g, 4.3119 mol). The hydrogenator was purged with $N_2$ (3×) and $H_2$ (3×). The reaction was pressured to 20 bar with hydrogen and stirred at room temperature overnight. The mixture was filtered through a pad of Celite (500 g) and washed with ethanol (2×0.6 L). The filtrate was concentrated. The residue was dissolved in DCM (1.8 L), dried over $MgSO_4$, filtered and concentrated. This gave the product VII as a clear oil (580 g, 94% yield).

(ii) Compound VI

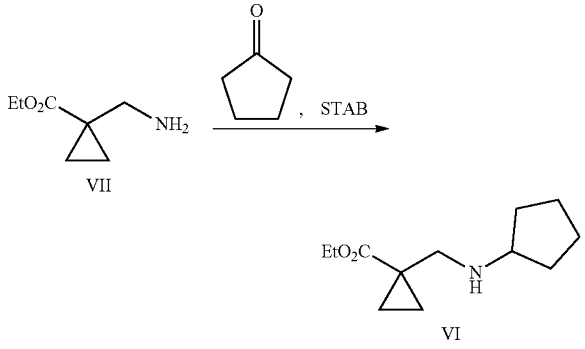

To a solution of the amine VII (800 g, 5.5874 mol) and cyclopentanone (520 ml, 5.867 mol) in DCM (8 L) was added $NaBH(OAc)_3$ (1777 g, 8.381 mol) at room temperature portionwise over ~1.5 h. The reaction mixture was then stirred at room temperature overnight. To decompose the excess of the reducing agent a saturated solution of $K_2CO_3$ in water (8 L) was added and the reaction mixture was stirred for 1 h at RT (gas evolution, pH=8). The layers were separated and the aqueous layer was extracted with DCM (4 L). The combined organic layers were washed with $K_2CO_3$aq (4 L), dried over $MgSO_4$, filtered and concentrated. This gave 1210.3 g of the product VI as a clear oil (1157 g active (contained 4.3% DCM), 98% yield).

(iii) Compound V

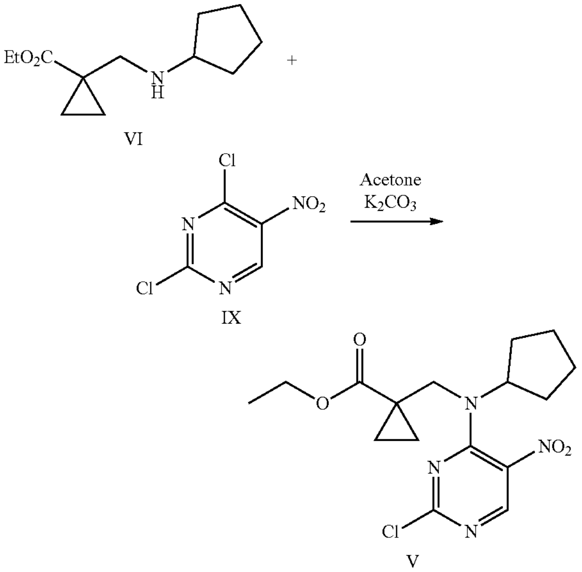

VI

IX

V

A solution of 2,4-dichloro-5-nitropyrimidine IX (1309.4 g, 6.750 mol) in acetone (11.4 L) was cooled to 0-5° C. and $K_2CO_3$ (933 g, 6.750 mol) was added. A solution of the amine VI (1426.3 g, 6.750 mol) in acetone (2.9 L) was then added dropwise over 1.5 h maintaining the temperature below 5° C. After 1 h, $^1$HNMR analysis showed ~6% of 2,4-dichloro-5-nitropyrimidine and no compound VI. Compound VI (86 g, 0.407 mol) in acetone (50 ml) was added and the mixture was stirred at RT for 1 h. The solids were filtered off and washed with acetone (1 L). The filtrate was concentrated at 25° C. (at higher temperatures the product polymerizes), the residue was dissolved in DCM (8 L), washed with water (2 L), dried over $MgSO_4$, filtered and concentrated at 25° C. This gave the product as an orange oily solid (2755 g, LC 85% pure). The product was suspended in $Et_2O$ (475 ml) and stirred at room temperature for 15 min. Heptane (475 ml) was added and the suspension was stirred for 1 h at room temperature. After that time the mixture was filtered, the filter cake was washed with $Et_2O$/heptane (1:1, 2×950 ml) and dried at 25° C. in a vacuum oven overnight. This gave 1762.2 g of the product V as a yellow solid (71% yield, LC 96.99% pure).

(iv) Compound IV

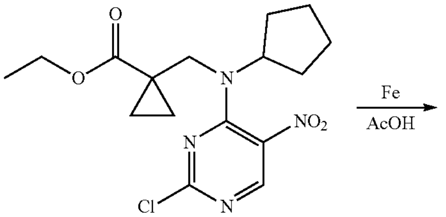

V

-continued

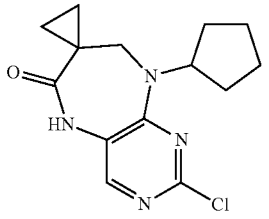

IV

AcOH (7.6 L) was heated to 60° C. and the heating mantle was removed. Fe powder (431 g, 7.727 mol) was added portionwise at 60° C. over 15 min (no exotherm, small gas evolution). The mixture was then cooled to 25° C. (ice bath) and compound V (950 g, 2.576 mol) was added portionwise over 3 h (small exotherm observed, cooled with ice/water, reaction temp maintained between 25-30° C.). The reaction mixture was stirred overnight at 25° C. After that time LC completion check indicated 82.0% product. The mixture was diluted with water (15.2 L, no exotherm) and the product was filtered off using filter cloth. The filter cake was washed with water (500 ml) then treated with saturated $NaHCO_3$aq (2 L, gas evolution). The solids were filtered off (filter paper) and washed with water (3×500 ml). The damp cake (1717 g) was combined with three batches of compound IV prepared by the same method [batch 1 (950 g)-1668 g water wet, batch 2 (950 g)-1701 g water wet, batch 3 (581.1 g) 1113 g water wet] and stirred in water (5 L) for 1 h at room temperature. The solids were filtered off and dried at 50° C. for 5 days in a vacuum oven. This gave 2972.4 g of compound IV as a brown solid (~100% yield, LC purity 94.5%, KF 0.65%, contains Fe salts). The product was used in the next stage without purification.

(v) Compound III

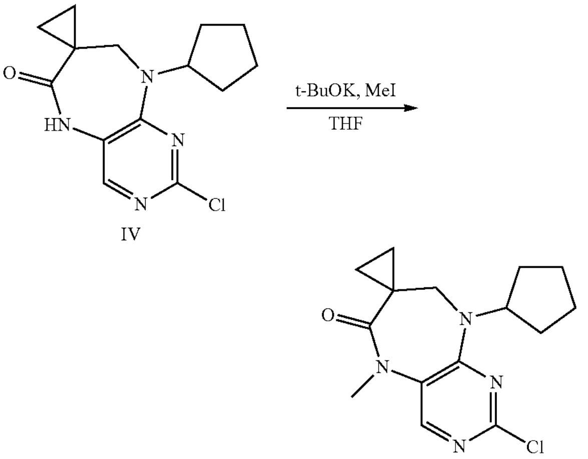

IV

III

Compound IV (2019.1 g gross, 1850.0 g active—assumed 100% yield in previous step) was added portionwise over 10 minutes within the specified range of 0-10° C. to a suspension of t-BuOK (854.3 g) in THF (19.0 L). The reaction mixture was stirred for 30 minutes within the specified range of 0-10° C. (final temperature 5.47° C.) then methyl iodide (440 ml) was added dropwise over 23 minutes maintaining the temperature within the specified range of 0-5° C. The mixture was stirred within the specified range of 0-5° C. for 15 minutes and then warmed to 20° C. over 2.5 hours and then stirred within the specified range of 20-25° C. overnight (12 hours). Completion analysis by HPLC showed that the reaction was complete (0.5% compound IV remaining, target not more than 1.0% remaining). The salts were filtered off and washed with THF (1920 mL). The filtrate was concentrated in vacuo and the residue (2321.2 g) was partitioned between DCM (5770 mL) and water (1150 mL). The organic layer was dried over $MgSO_4$ (426.2 g) filtered, washed with DCM (1000 mL) and concentrated in vacuo. This gave the product as a pale yellow solid (1924.3 g) which was oven dried at 40° C. for 24 hours to give compound III. Yield=(1502.2 g, 77.5%). Material 98.48% pure by HPLC (0.0% compound IV).

1.2 Synthesis of Trans-Compound XI

(i) Synthesis of Trans-Compound XII by Reductive Amination

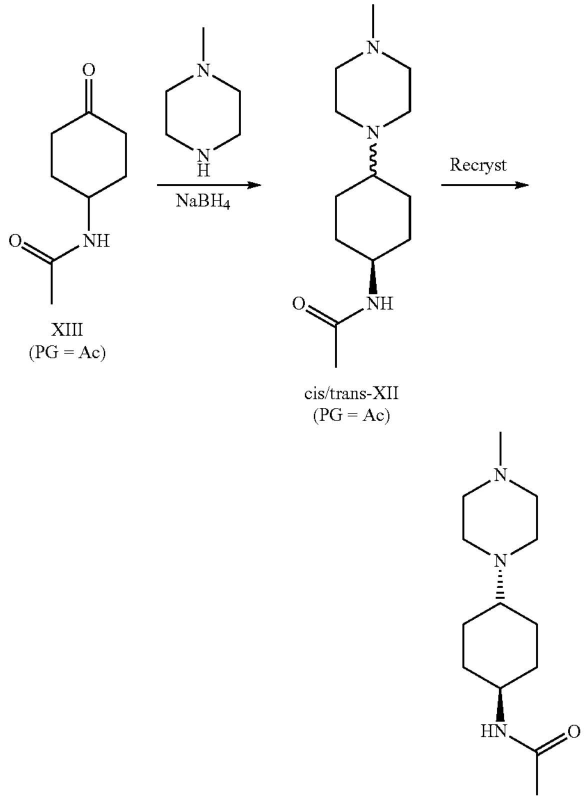

XIII (PG = Ac)

cis/trans-XII (PG = Ac)

trans-XII (PG = Ac)

4-Acetamidocyclohexanone XIII (850 g, 5.477 mol), N-methylpiperazine (729 ml, 6.573 mol) and $MeSO_3H$ (28.5 ml, 0.438) in toluene (6.8 L) were heated for 5 h at reflux employing a Dean & Stark separator (94 ml of water was collected). The skilled person would understand that alternative amine protecting groups could be used in compound XIII, e.g. BOC, $Bn_2$ and the like. After that time the mixture was cooled to 50° C. (at lower temperatures mixture solidifies) and diluted with EtOH (6.8 L). The intermediate enamine was treated with $NaBH_4$ (207.2 g, 5.477 mol) portionwise at 15-20° C. and stirred at room temperature overnight. The excess of $NaBH_4$ was decomposed with 6M HCl (4 L) at 10-15° C. The skilled person would understand that alternative reducing agents could be used, e.g. $LiBH_4$ instead of $NaBH_4$. The layers were separated and the aqueous layer was treated with $K_2CO_3$ (1.2 kg, to achieve pH=8). The solids were filtered off and washed with DCM (2.5 L, this was used later for the extraction). The filtrate was concentrated. The residue was extracted with DCM (2×2.5 L), basified with 1.25M KOH (200 ml, to pH=10) and extracted with DCM (2.5 L). The combined organic layers were dried over $MgSO_4$, filtered and concentrated. The crude product (1020 g) was combined with 3792 g of the product from batches 1-3 prepared by the same method and purified on basic alumina (16.5 kg) eluting with 50% heptane/DCM (16 L), 75% heptane/DCM (32 L), DCM (40 L) then 10 L 1% MeOH/DCM. This gave the product as a white solid (2410 g, 47% yield, cis:trans ratio 36:64).

The product was combined with 753.7 g of cis/trans product, dissolved in MeCN (9.32 L) at reflux and allowed to cool to RT overnight. The suspension was cooled to 5-10° C. and stirred for 2 h. The precipitate was filtered off, washed with MeCN (1×3.1 L, 1×2 L and 1×1 L) and pulled dry on the filter. The product was dried at 45° C. overnight. This gave 544.9 g of the product trans-XII as a white solid (1613.2 g, ~25% yield, >95% pure by $^{1}H$ NMR, cis isomer not detected by $^{1}H$ NMR).

(ii) Compound Trans-XI

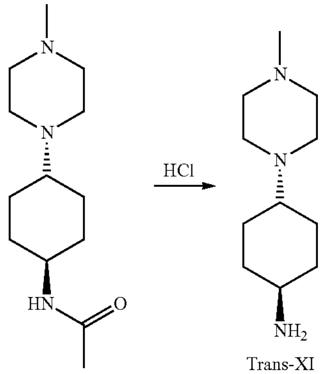

Trans-XII

Trans-XI

Concentrated hydrochloric acid (4500 mL) was added over 5 minutes to water for irrigation (2240 mL) maintaining a temperature within the specified range of 20-40° C. (final temp 23.83° C.). Trans-XII (1100.9 g) was added over 4 minutes and the reaction was then heated to 105° C. over 60 minutes. The reaction was heated at 95-106° C. overnight (17.5 hours) by which time an in-process check by $^{1}H$ NMR showed that the reaction was complete. The reaction mixture was cooled to within the specified range of 15-25° C. over 72 minutes. Solid potassium hydroxide (5890.1 g) was added in portions over approximately 1 hour maintaining the temperature within the specified range of 20-45° C. to give a final pH of 12. The reaction mixture was cooled to within the specified range of 15-25° C. over 5 minutes and stirred at within the specified range of 15-25° C. overnight (17.5 hours) (final temperature 17.97° C.). The suspension was filtered and the filter cake washed with THF (6120 mL×3 then 4080 mL). The combined filtrate was returned to the vessel and the phases separated. The organic phase was concentrated in vacuo in portions to give 1287.4 g of material. The residual water was removed by azeotroping with toluene (2025 mL, then 2020 mL). The product was then dissolved in DCM (2000 mL), the solids were filtered off (a small amount of inorganic material was removed), washed with DCM (200 ml) and the filtrate was concentrated in vacuo. This gave the product as low melting solid (939.1 g, quantitative yield, active yield (by $^1$H NMR) 888.4 g, 97.9%). 4.59% toluene and 0.81% DCM by $^1$H NMR, 90.1% trans-XI by HRGC.

1.3 Alternative Synthesis of Trans-Compound XI

Alternatively, the reductive amination step can be carried out as follows:

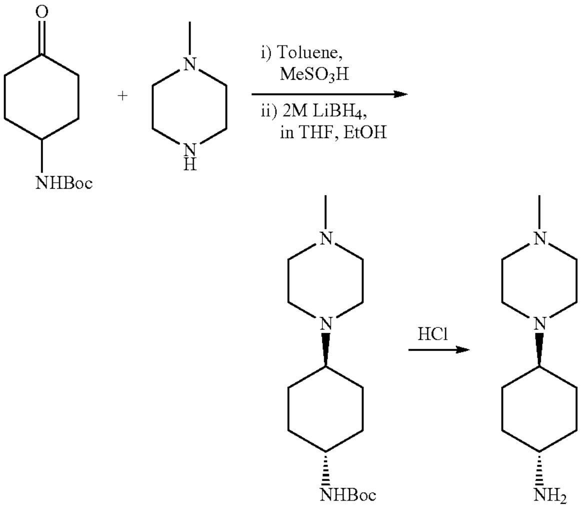

Trans-XI

Boc-4-aminocyclohexanone (20 g, 93.8 mmol), followed by N-methylpiperazine (13 mL, 117.2 mmol), methanesulfonic acid (0.5 mL, 7.7 mmol) and toluene (140 mL) were added to a flask at RT under $N_2$. The slurry was heated over 30 mins to reflux in a Dean-Stark set up [no exotherm noted upon warming] and a pale brown solution formed. The solution was stirred at 110° C. to 115° C. for 6 h to remove $H_2O$. and at this point, $^1$H NMR showed 83% enamine. The solution was cooled to 50° C. over 20 min (using an ice/water bath) and EtOH (100 mL) was added. The solution was then further cooled to 20° C. over 20 min and $LiBH_4$ (2M in THF, 100 mL, 200.0 mmol) was added dropwise over 30 min [exotherm 20-27° C. and significant off-gassing observed]. The reaction was left to stir at RT for 18 h. At this point, $^1$H NMR showed <5% enamine. The reaction was quenched via dropwise addition of 6M HCl (~150 mL, 900.0 mmol) [exotherm 20-25° C. and minor off-gassing] over 15 mins until pH 2 was observed. The phases were separated, and the organic layer was removed. The aqueous was then basified via addition of $K_2CO_3$(s) (30 g, 217.1 mmol) over 15 mins [exotherm 20-28° C. and significant off-gassing] until pH 8 was reached. The slurry was filtered, and the filtrate was reduced in vacuo to give a pale brown oil. The filter cake was washed with DCM (2×80 mL). The brown oil-was partitioned between the DCM from the filter-cake washing and 2M NaOH (20 mL). The aqueous was removed and extracted with DCM (90 mL). The combined DCM extracts were dried ($MgSO_4$), filtered and reduced in vacuo to give a pale orange oil. The oil was azeotroped with MeCN (100 mL) to give 23 g of a beige solid (82% crude yield). $^1$H NMR that showed ~75/25 ratio of trans to cis and an overall purity of ~50%. An 11 g portion of the solid was slurried in MeCN (55 mL) and heated to 70° C. [a solution formed at 67° C.], then cooled to RT over 1 h. The slurry was stirred at RT for 18 h. The slurry was filtered, washed (MeCN, 5 mL) and dried in vacuo to give 4.3 g of the trans Boc-protected product (32% yield) as a white powder at 95% purity by $^1$H NMR with <1% cis.

The trans Boc-protected product was then deprotected by treatment with concentrated HCl under the same conditions set forth above in Section 1.2 (ii) to form trans-XI.

1.4 Synthesis of Compound I (i) Compound II

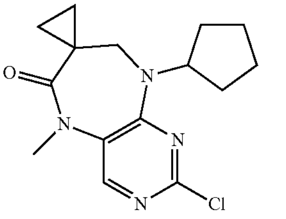

+

III
$C_{15}H_{19}ClN_4O$
Exact Mass: 306.12
Mol. Wt.: 306.79

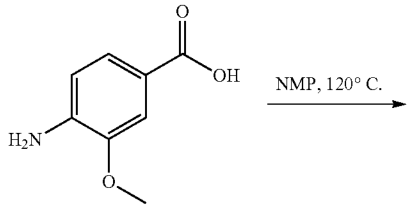

X
$C_8H_9NO_3$
Exact Mass: 167.06
Mol. Wt.: 167.16

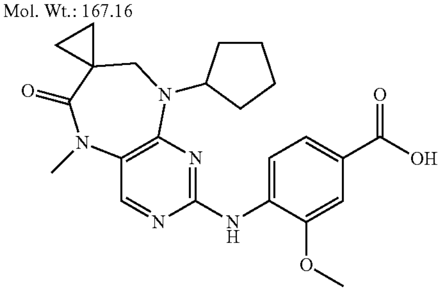

II
$C_{23}H_{27}N_5O_4$
Exact Mass: 437.21
Mol. Wt.: 437.49

A solution of compound III (1490.6 g active, 1492.7 g gross) and compound X (898.9 g) in NMP (2960 mL) was heated to within the specified range of 115-125° C. over 51 minutes and then heated within the range 115-125° C. for 36 h. The batch was cooled with stirring for 4 hours after which time it was left to cool without stirring (when cooled the batch contains a significant quantity of solid which does not stir easily). After standing for almost 29 hours the batch was warmed to 52° C. to allow the batch to be sampled as a mobile homogenous suspension. Analysis by HPLC showed that the reaction was complete (83.35% compound II present, target GT 75%). The batch was cooled to 20° C. and the mixture was diluted with water for irrigation (6000 mL) with a moderate exotherm being observed which caused the batch to warm to 26.8° C., external cooling was applied and the batch was then stirred at within the specified range of 10-25° C. for 40 minutes, the product was filtered, washed with water for irrigation (2×1500 mL), pulled dry and oven dried within the specified range of 45-55° C. for 18-20 hours by which time the product in each of the three oven drying trays showed a water content of LT 10% (by KF analysis). The crude product (2212.7 g) was slurried in toluene (6630 mL) for 74 minutes at 10-25° C. (final temp 18.3° C.) in order to remove unreacted compound III. The solid was filtered, washed with toluene (1520 mL) and oven dried within the specified range of 45-55° C. for 17 hours. In-process analysis on the solid in each of the three oven drying trays showed 0.21-0.35% compound III by HPLC (target LT 0.5%); 1.56-1.85% NMP by $^1$H NMR (target NMT 2.5%) with toluene not detected by 1H NMR (result FOI). The solid was then packaged. Yield 1905.8 g (89.7% yield). 93.16% pure by HPLC (0.30% compound III).

(ii) Compound I

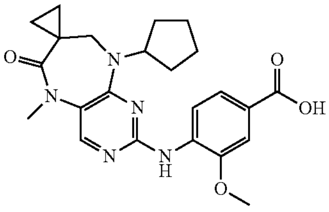

II
$C_{23}H_{27}N_5O_4$
Exact Mass: 437.21
Mol. Wt.: 437.49

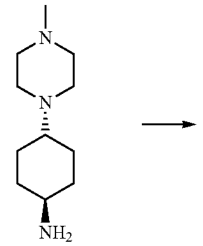

trans-XI
$C_{11}H_{23}N_3$
Exact Mass: 197.19
Mol. Wt.: 197.32

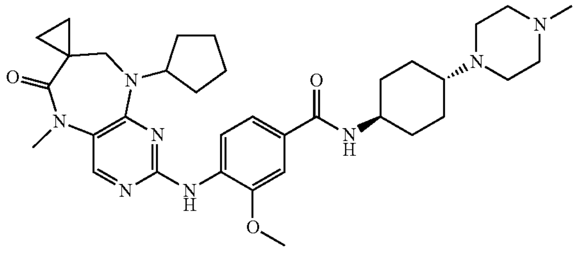

I
$C_{34}H_{48}N_8O_3$
Exact Mass: 616.38
Mol. Wt.: 616.8

To a suspension of compound II (1869.8 g active, 1896.5 g gross) in DCM (18640 mL) was added HBTU (1801.9 g) rinsing in with DCM (20 mL) within the specified range of 15-25° C. DIPEA (1500 mL) was then added dropwise at within the specified range of 15-25° C. The reaction mixture was stirred with the specified range of 15-25° C. for 31 minutes by which time analysis by TLC indicated complete consumption of compound II. Trans-Compound XI (905.1 g) was added portionwise over 30 minutes maintaining the temperature within the specified range of 15-25° C. The reaction mixture was stirred within the specified range of 15-25° C. for 69 minutes. The batch was then sampled and analysis by HPLC showed 0.02% compound II remaining (target LT 0.5%). The mixture was washed with NaOH solution (9440 mL, then 9400 mL, then 9420 mL, 0.4M NaOH) and water (9400 mL) in order to remove HOBt. After the final wash in-process analysis indicated 0.05% HOBt by HPLC (target LT 1%). It was noted that a significant quantity of solid had precipitated in the organic layer. The organic layer could not immediately be dried over $MgSO_4$ since the solid would be lost during filtration. The suspension in the organic phase was filtered and the filter cake washed with DCM (500 mL). The filtrate was then dried over $MgSO_4$ (1284.3 g) filtered and washed with DCM (1500 mL). The organics were then concentrated in vacuo at 40° C. The filtered solid was then added to give 3489.9 g of solid. The crude product (in 6 flasks) was evaporated from EtOAc (total 6500 mL). The product was returned to the 50 L vessel and slurried in EtOAc (8500 mL) at within the specified range of 10-25° C. for 36 minutes, filtered, washed with EtOAc (2160 mL, then 2150 mL) and dried at within the specified range of 45-55° C. for 64.5 hours. This gave 2475.3 g of the product (0% EtOAc, 10.6% DCM by 1HNMR). The product was dissolved in MeOH (5980 mL) at within the specified range of 60-70° C. (final temperature 62.7° C.). The solution was immediately polish filtered into the 50 L vessel (final temperature 54.17° C.). The solution was warmed-up to within the specified range of 60-70° C. (final temperature 60.3° C.). Water for irrigation (5760 mL) was added dropwise over 39 minutes maintaining temperature within the specified range of 60-70° C. The mixture was stirred at within the specified range of 60-70° C. for 10 minutes and was then cooled to 25° C. over 123 minutes. After stirring at within the specified range of 15-25° C. for 21 minutes (final temperature 19.16° C.) the suspension was filtered, washed with a (1:1) solution of MeOH in water for irrigation (2880 mL, then 2700 mL), pulled dry on the filter and oven dried at within the specified range of 45-55° C. for 19.5 hours to give 2076.3 g (78.8% yield) of product. 96.43% pure by HPLC (0.33% compound I cis, 0.01% compound II, 0.01% HOBt, specification NLT 95.0%); 2.75% water by KF.

Comparative Example (as Per WO 2009/040556)

(i) 4-(4-methylpiperazin-1-yl)cyclohexanamine

N-benzyloxycarbonyl-4-aminocyclohexanone (1 mmol) was added to a reaction tube containing THF (5 mL), N-methylpiperazine, acetic acid and sodium triacetoxyborohydride. The reaction was stirred at ambient temperature for 20 hours. The reaction was quenched with $NaHCO_3$ solution (2 mL) before acidifying to pH2 with 1N HCl solution. The mixture was washed with EtOAc before separating the aqueous layer and basifying to pH10 with 2N NaOH solution. The product was extracted into EtOAc, which was washed with sat. NaCl, dried ($MgSO_4$) and evaporated under reduced pressure. The product so formed was dissolved in methanol to a concentration of 0.05M. Hydrogenation was conducted using an H-Cube™ (ThalesNano Inc.) flow reactor at 1 mL/min flow rate over 10% Pd/C catalyst heated 5 to 60° C. under full hydrogen mode. Concentration under reduced pressure provided 4-(4-methylpiperazin-1-yl)cyclohexanamine.

(ii) Compound I

Compound III (66 mg, 0.15 mmol, 1 eq), DIPEA (52 µl, 0.3 mmol, 2 eq) and TBTU (54 mg, 0.17 mmol, 1.1 eq) were added to 1 mL DMF and the resulting solution was stirred at room temperature for 20 min before the addition of 4-(4-methylpiperazin-1-yl) cyclohexanamine (35 mg, 0.18 mmol, 1.2 eq) dissolved in DMF (0.5 mL). The reaction mixture was then stirred at room temperature for 2 hours before purifying by preparative RP-HPLC-MS to provide compound I as a white solid (17 mg, 18%).

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

The invention claimed is:

1. A process for preparing a compound of formula (XII), wherein PG is a protecting group selected from the group consisting of acetyl and tert-butoxycarbonyl (BOC), or a compound of formula (XI), comprising the steps of:

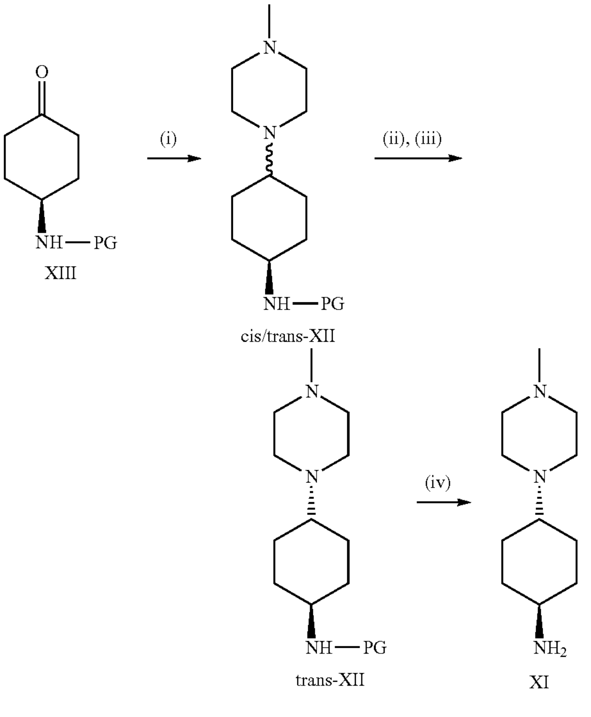

XIII
cis/trans-XII
trans-XII
XI (i) treating a compound of formula XIII, wherein PG is a protecting group selected from the group consisting of acetyl and tert-butoxycarbonyl (BOC), with N-methylpiperazine to form a compound of formula XII, wherein said compound of formula XII is in the form of a mixture of cis and trans isomers;

(ii) combining the mixture formed in step (i) with an organic solvent and heating the solvent mixture so formed;

(iii) isolating the trans-isomer of the compound of formula XII from the solvent mixture formed in step (ii); wherein step (iii) comprises cooling the mixture such that the trans-isomer of the compound of formula XII precipitates out of solution, filtering the precipitate so formed, and optionally washing and/or drying the precipitate; and (iv) optionally treating said trans-isomer of the compound of formula XII with an acid to form a compound of formula XI; and isolating said compound of formula XI.

2. The process according to claim 1, wherein step (i) comprises the steps of:

(a) forming a mixture comprising a compound of formula XIII, N-methylpiperazine, a solvent and an acid, and heating said mixture;

(b) cooling the mixture obtained in step (a), and diluting with a solvent;

(d) treating the mixture obtained in step (b) with a reducing agent; and (e) isolating the compound of formula XII as a mixture of cis and trans isomers.

3. The process according to claim 2, wherein the reducing agent in step (d) is $NaBH_4$ or $LiBH_4$.

4. The process according to claim 2, wherein the solvent in step (i)(a) is toluene, and the acid is a sulfonic acid selected from benzene sulfonic acid, para-toluene sulfonic acid and methanesulfonic acid.

5. The process according to claim 1, wherein the organic solvent in step (ii) is acetonitrile.

6. The process according to claim 1, wherein step (ii) comprises heating the solvent mixture.

7. The process according to claim 1, wherein step (iii) comprises cooling the mixture to a temperature of from 0 to about 15° C.

8. The process according to claim 1, wherein the compound of formula XII obtained in step (iii) is substantially free from the cis-isomer.

9. The process according to claim 1, which comprises the step of treating said compound of formula XII with an acid to form a compound of formula XI.

10. A process of preparing a compound of formula I, or a pharmaceutically acceptable salt thereof, which comprises the steps of:

(I) preparing a compound of formula XI by the process according to claim 1;

(II) contacting said compound of formula XI with a compound of formula II to form a compound of formula I;

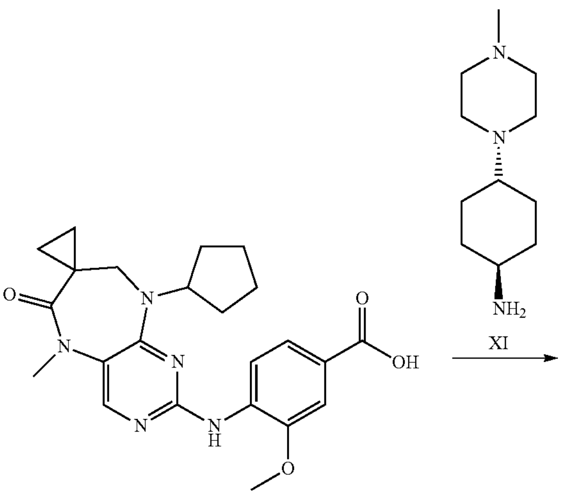
II
XI

-continued

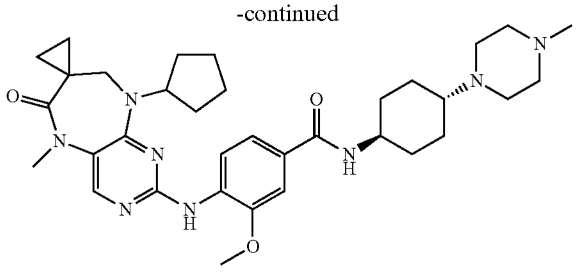

I (III) isolating the compound of formula I; and (IV) optionally converting said compound of formula I to a pharmaceutically acceptable salt form thereof.

11. The process according to claim 10, wherein said compound of formula XI is substantially free from the cis-isomer.

12. The process according to claim 10, wherein step (II) is carried out in the presence of dichloromethane, N,N-diisopropylethylamine (DIPEA) and (2-(1H-benzotriazol-1-yl)-1, 1,3,3-tetramethyluronium hexafluorophosphate (HBTU).

13. The process according to claim 10, which further comprises preparing a compound of formula II by a reaction which comprises contacting a compound of formula III with a compound of formula X:

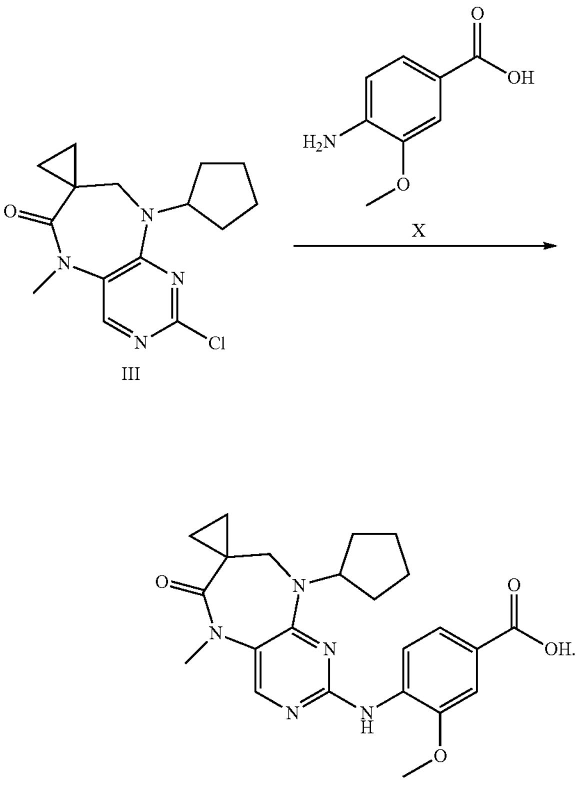

X

III

II

14. The process according to claim 13, which further comprises preparing a compound of formula III by a reaction which comprises treating a compound of formula IV with MeI

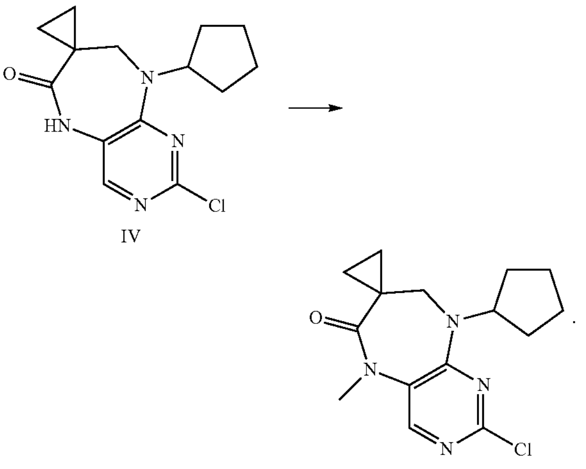

IV

III

15. The process according to claim 14, which further comprises preparing a compound of formula IV by a reaction which comprises treating a compound of formula V with Fe powder in the presence of acetic acid:

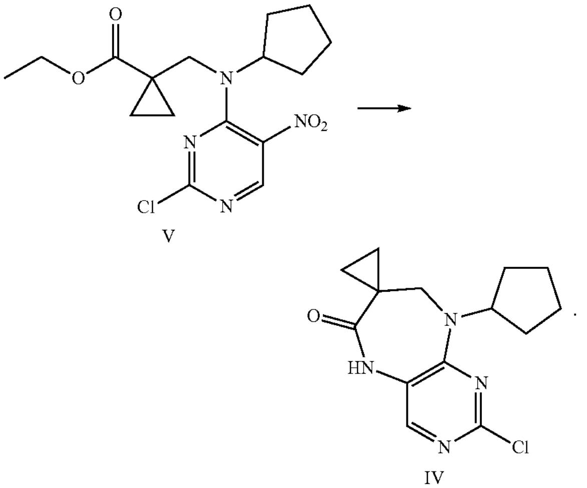

V

IV

16. The process according to claim 15, which further comprises preparing a compound of formula V by a reaction which comprises contacting a compound of formula VI with a compound of formula IX:

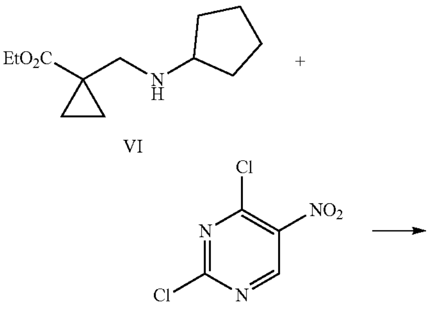

VI

IX

-continued

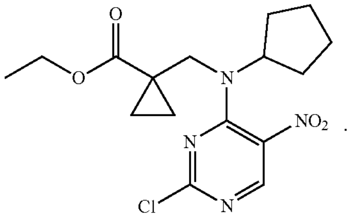

V

17. The process according to claim 16, which further comprises preparing a compound of formula VI by a reaction which comprises contacting a compound of formula VII with cyclopentanone in the presence of a reducing agent:

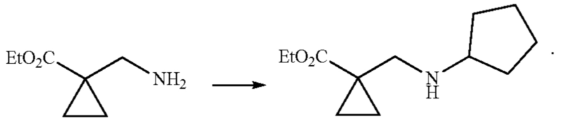

VII VI

18. The process according to claim 17, which further comprises preparing a compound of formula VII by hydrogenating a compound of formula VIII in the presence of a solvent and Raney nickel catalyst:

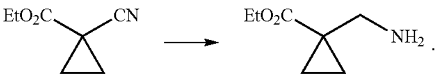

VIII VII

19. A process of preparing a compound of formula I, or a pharmaceutically acceptable salt thereof, which comprises the steps of:

(A) hydrogenating a compound of formula VIII in the presence of Raney nickel catalyst to form a compound of formula VII;

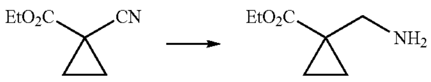

VIII VII (B) contacting said compound of formula VII with cyclopentanone to form a compound of formula VI;

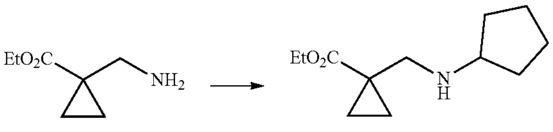

VII VI (C) contacting said compound of formula VI with a compound of formula IX to form a compound of formula V;

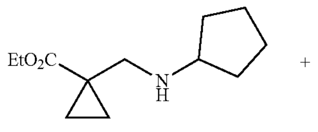

VI

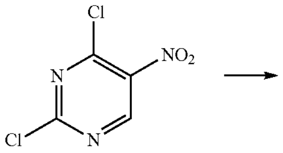

IX

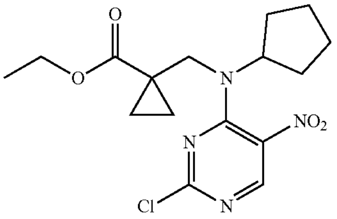

V (D) treating said compound ot formula V with He powder in the presence of acetic acid to form a compound of formula IV;

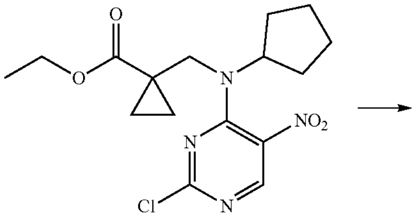

V

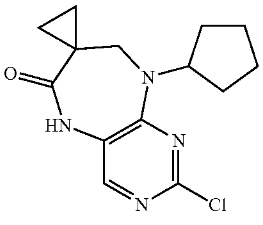

IV (E) treating said compound of formula IV with MeI to form a compound of formula III;

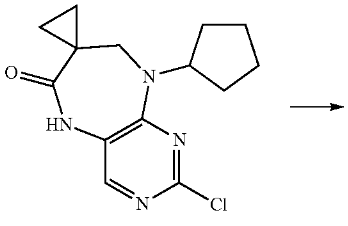

IV

-continued

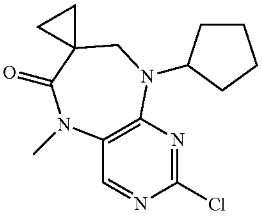

III (F) contacting said compound of formula III with a compound of formula X to form a compound of formula II;

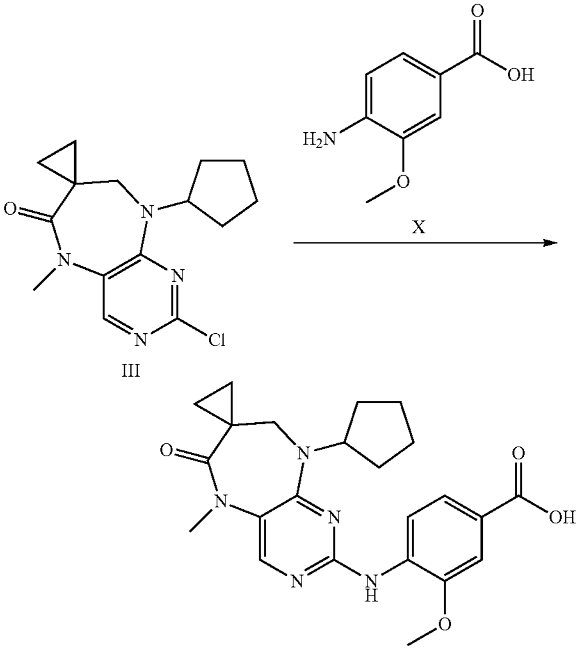

X

III

II (G) contacting said compound of formula II with a compound of formula XI to form a compound of formula I;

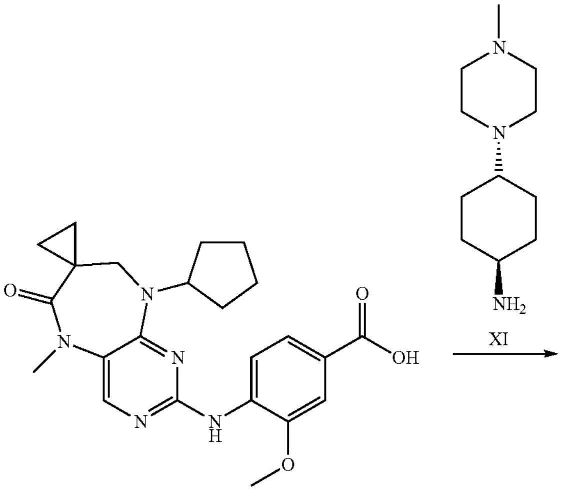

XI

II

-continued

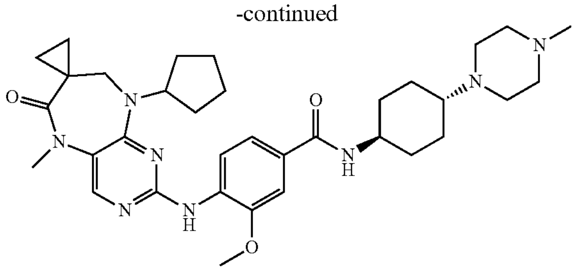

I (H) isolating the compound of formula I; and (I) optionally converting said compound of formula I to a pharmaceutically acceptable salt form thereof.

20. The process according to claim 19, wherein said compound of formula XI is prepared by a process comprising the steps of:

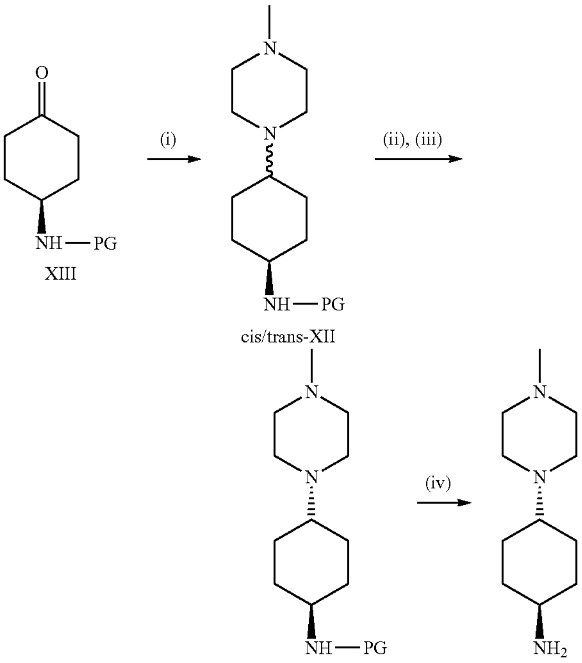

XIII cis/trans-XII trans-XII

XI (i) treating a compound of formula XIII, wherein PG is a protecting group selected from the group consisting of acetyl and tert-butoxycarbonyl (BOC), with N-methylpiperazine to form a compound of formula XII, wherein said compound of formula XII is in the form of a mixture of cis and trans isomers;

(ii) combining the mixture formed in step (i) with an organic solvent and heating the solvent mixture so formed;

(iii) isolating the trans-isomer of the compound of formula XII from the solvent mixture formed in step (ii); wherein step (iii) comprises cooling the mixture such that the trans-isomer of the compound of formula XII precipitates out of solution, filtering the precipitate so formed, and optionally washing and/or drying the precipitate; and (iv) treating said trans-isomer of the compound of formula XII with an acid to form a compound of formula XI; and isolating said compound of formula XI.

* * * * *